United States Patent
Gunasekaran et al.

(10) Patent No.: US 10,684,249 B2
(45) Date of Patent: Jun. 16, 2020

(54) CONTAMINANT DETECTION DEVICE AND METHOD

(71) Applicant: UWM Research Foundation, Inc., Milwaukee, WI (US)

(72) Inventors: Sundaram Gunasekaran, Madison, WI (US); Woo-Jin Chang, Whitefish Bay, WI (US); Jiang Yang, New York, NY (US); Rajesh Seenivasan, Madison, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 387 days.

(21) Appl. No.: 15/529,211

(22) PCT Filed: Dec. 3, 2015

(86) PCT No.: PCT/US2015/063809
§ 371 (c)(1),
(2) Date: May 24, 2017

(87) PCT Pub. No.: WO2016/090176
PCT Pub. Date: Jun. 9, 2016

(65) Prior Publication Data
US 2017/0363572 A1    Dec. 21, 2017

Related U.S. Application Data

(60) Provisional application No. 62/087,032, filed on Dec. 3, 2014, provisional application No. 62/145,826, filed on Apr. 10, 2015.

(51) Int. Cl.
*G01N 27/327*    (2006.01)
*G01N 27/411*    (2006.01)
(Continued)

(52) U.S. Cl.
CPC ....... *G01N 27/4115* (2013.01); *G01N 27/301* (2013.01); *G01N 27/302* (2013.01);
(Continued)

(58) Field of Classification Search
CPC ............. G01N 27/4115; G01N 27/301; G01N 27/302; G01N 27/308; G01N 27/4148;
(Continued)

(56) References Cited

U.S. PATENT DOCUMENTS

2001/0032785 A1   10/2001   Cha et al.
2007/0252715 A1   11/2007   Reddy et al.
(Continued)

FOREIGN PATENT DOCUMENTS

CN   101754813 A   6/2010
CN   102220597 A   10/2011
(Continued)

OTHER PUBLICATIONS

Z.-Q. Zhao, et al. "Selective adsorption toward toxic metal ions results in selective response: electrochemical studies on a polypyrrole/reduced graphene oxide nanocomposite", Chem Commun., 48(16), p. 2180-2182 + S1-S5 (Year: 2012).*
(Continued)

*Primary Examiner* — J. Christopher Ball
(74) *Attorney, Agent, or Firm* — Michael Best & Friedrich LLP

(57) ABSTRACT

A device for measuring pH levels and contaminant concentration includes an electrode assembly that is electrically coupled to a control unit. The electrode assembly includes a first contact electrically coupled to a reference electrode, a second contact electrically coupled to a working electrode, and a third contact electrically coupled to a counter electrode. The working electrode may be modified to include a cysteine functionalized graphene oxide with polypyrrole
(Continued)

nanocomposite. In operation, the control unit may apply a complex signal to the working electrode via the second contact in order to adhere and subsequently strip contaminant ions from the fluid sample to the working electrode. During this process, a current may be measured across the working electrode and the counter electrode to measure contaminant ion concentration. The pH of the fluid sample may also be determined by a current measured across the reference electrode and the counter electrode. In some examples, the pH may be used to calibrate the measured levels of the contaminant ions.

19 Claims, 19 Drawing Sheets

(51) Int. Cl.
G01N 27/42 (2006.01)
G01N 27/416 (2006.01)
G01N 27/30 (2006.01)
G01N 27/414 (2006.01)
G01N 33/18 (2006.01)
G01N 27/333 (2006.01)

(52) U.S. Cl.
CPC ....... G01N 27/308 (2013.01); G01N 27/4148 (2013.01); G01N 27/4167 (2013.01); G01N 27/42 (2013.01); G01N 27/333 (2013.01); G01N 33/1813 (2013.01)

(58) Field of Classification Search
CPC ............. G01N 27/333; G01N 33/1813; G01N 27/4167; G01N 27/42
See application file for complete search history.

(56) References Cited

U.S. PATENT DOCUMENTS

2007/0278096 A1 12/2007 Viltchinskaia et al.
2008/0206876 A1 8/2008 Kanzer et al.
2010/0233824 A1 9/2010 Verhoeckx et al.

FOREIGN PATENT DOCUMENTS

| CN | 103454333 A | 12/2013 |
| CN | 203484166 U | 3/2014 |
| CN | 104022263 A | 9/2014 |
| EP | 0929804 B1 | 4/2007 |
| WO | 2007/007078 A2 | 1/2007 |
| WO | 2008046086 A2 | 4/2008 |
| WO | 2014/096977 | 6/2014 |

OTHER PUBLICATIONS

European Patent Office Partial Supplementary European Search Report for Application No. 15865172.9 dated Aug. 9, 2018 (15 pages).
Muralikrishna et al., "In Situ Reduction and Functionalization of Graphene Oxide with L-Cysteine for Simultaneous Electrochemical Determination of Cadmium(II), Lead(II), Copper(II), and Mercury(II) ions," Analytical Methods, 2014, 6(21):8698-8705.
Seenivasan et al., "Highly Sensitive Detection and Removal of Lead Ions in Water Using Cysteine-Functionalized Graphene Oxide/Polypyrrole Nanocomposite Film Electrode," ACS Appl. Mater Interfaces, 2015, 7(29):15935-15943.
Zhao et al., "Selective adsorption toward toxic metal ions results in selective response: electrochemical studies on a polypyrrole/reduced graphene oxide nanocomposite," Chem. Commun., 2012, 48(16):2180-2182.
International Search Report and Written Opinion, PCT/US2015/063809, dated Mar. 22, 2016.
Aragay, et al, "Recent Trends in Macro-, Micro-, and Nanomaterial-Based Tools and Strategies for Heavy-Metal Detection," Chemical Reviews, 2011, 111, 3433-3458.
Aryal, et al, "Spectroscopic identification of S—Au interaction in cysteine capped gold nanoparticles," Spectrochimica Acta Part A, 2006, vol. 63: 160-163.
Atanassova, et al. "Preconcentration of trace elements on a support impregnated with sodium diethyldithiocarbamate prior to their determination by inductively coupled plasma-atomic emission spectrometry", Talanta, 1998, 45(5), 857-864.
Brett, "Electrochemical sensors for environmental monitoring. Strategy and examples", Pure Appl. Chemistry, 2001, vol. 73, No. 12, 1969-1977.
Cate, "Recent Developments in Paper-Based Microfluidic Devices,", Analytical Chemistry, 2014, vol. 87, 19-41.
Chandra, et al, "Highly Selective Adsorption of Hg2+ by a polypyrrole-reduced graphene oxide composite," Chemical Communications, 2011, 47, 3942-3844.
Chen, et al, "An environment-friendly preparation of reduced graphene oxide nanosheets via amino acid," Nanotechnology 2011, vol. 22, 325601.
Chen, et al., "A fluidic diode, valves, and a sequentialloading circuit fabricated on layered paper", Lab on a Chip, 2012, vol. 12, 2909-2913.
Chen, et al., "Square wave anodic stripping voltammetric determination of Cd and Pb ions at a Bi/Nafion/thiolated polyaniline/glassy carbon electrode," Electrochemistry Communications, 2012, 15, 34-37.
Choi, et al, "Heavy metal ion adsorption onto polypyrrole-impregnated prorous carbon," Journal of Colloid and Interface Science, 2008, vol. 325: 287-289.
Chouteau, et al., "Development of novel conductometric biosensors based on immobilized whole cell Chlorella vulgaris microalgae," Biosensensors & Bioelectronics, 2004, 19(9), 1089-1096.
Cote, et al, "Langmuir-Blodgett Assembly of Graphite Oxide Single Layers," Journal American Chemistry Society, 2009, 131, 1043.
Dikin, et al, "Preparation and characterization of graphene oxide paper," Nature, 2007, vol. 448, 457-460.
Eda, et al, "Chemically derived graphene oxide: Towards Large-Area Thin-Film Electronics and Optoelectronics," Advanced Materials 2010, vol. 22, 2392.
Fang et al., "IrOx and Pt—Ir electrochemical sensors: prospective enzyme less pH and glucose sensors for continuous monitoring in cell culture," IMCS—The 14th International meeting on chemical sensors (2012).
Faraji, et al., "Extraction of trace amounts of mercury with sodium dodecyle sulphate-coated magnetite nanoparticles and its determination by flow injection inductively coupled plasma-optical emission spectrometry", Talanta, 2010, vol. 81, 831-836.
Feng, "Using Nanostructured conductive carbon tape modified with bismuth as the disposable working electrode for stripping analysis in paper-based analytical devices," Talanta, 2013, vol. 115: 235-240.
Fu, et al., "Electrochemical determination of trace copper (II) with enhanced sensitivity and selectivity by gold nanoparticle/single-wall carbon nanotube hybrids containing three-dimensional L-cysteine molecular adapters," Sensors and Actuators B: Chemical, 2013, 182, 382-389.
Geim, et al., "The Rise of Graphene," Nature Publishing Group, 2007, vol. 6(3): 183-191.
Grieshaber, et al., "Electrochemical biosensors—Sensor principles and architectures," Sensors, 2008, vol. 8, 1400-1458.
Hogue, "Clearing the water," Chemical Engineering News, Mar. 2000, p. 31-33.
Hummers, et al, "Preparation of Graphitic Oxide," Journal American Chemical Society, 1958, 80, 1339.
Izumi, "X-ray Absorption Fine Structure Combined with Fluorescence Spectrometry for Monitoring Trace Amounts of Lead Adsorption in the Environmental Conditions," Analytical Chemistry, 202, vol. 74, 3819-3823.

(56) References Cited

OTHER PUBLICATIONS

Jarup, "Hazards of heavy metal contamination," British Medical Bulletin, 2003, vol. 68: 167-182.

Kampouris et al., "Screen printed electrochemical platforms for pH sensing," Analytical Methods 1: 25-28 (2009).

Khaled, et al., "Chitosan modified screen-printed carbon electrode for sensitive analysis of heavy metals," International Journal of Electrochemistry Science, 2010, vol. 5, 158-167.

Kurzweil, "Metal Oxides and ion-exchanging surfaces at pH sensors in liquids: state of the art and outlook," Sensors 9:4955-4985 (2009).

Li et al., "A perspective on paper-based microfluidics: current status and future trends," Biomicrofluidics 6: 011301 (2012).

Li, et al, "Nafion-graphene nanocomposite film as enhanced sensing platform for ultrasensitive determination of cadmium," Electrochemistry Communications 2009, vol. 11, 1085-1088.

Li, et al, "Supramolecular solvent-based microextraction of copper and lead in water samples prior to reacting with synthesized Schiff base by flame atomic absorption spectrometry determination," Analytical Methods, 2014, vol. 6: 2294-2298.

Liana,et al, "Recent Advances in paper-based sensors," Sensors, vol. 12: 11505-11526 (2012).

Lin, et al, "Determination of As, Cd, Hg, and Pb in herbs using slurry sampling electrothermal vaporization inductively couple plasma mass," Food Chemistry, 2013, vol. 141: 2158-2162.

Liu, et al., "A Graphene Oxide Streptavidin Complex for Biorecognition—Towards Affinity Purification," Advanced Functional Materials, 2010, 20, 2857-2865.

Luo et al., "High Yield Preparation of Macroscopic Graphene Oxide Membranes" Journal of American Chemical Society, Jan. 2009, 131, pp. 898-899.

Mentele, et al., "Microfluidic paper-based analytical device for particulate metals", Analytical Chemistry, 2012, vol. 84, 4474-4480.

Morton, et al., "Detection of Trace Heavy Metal Ions Using Carbon Nanotube-Modified Electrodes," Electroanalysis, 2009, vol. 21, No. 14, 1597-1603.

Musa et al., Disposable Miniaturized Screen-Printed pH and Reference Electrodes for Potentiometric Systems. Electroanalysis 23(1): 115-121 (2011).

Navas-Acien, et al, "Lead Exposure and Cardiovascular Disease—A Systematic Review," Environ. Health Perspect. 2007, 115, 472.

Nie, "Electrochemical sensing in paper-based microfluidic devices," Lab Chip, 2010, 10, 477-483.

Nie, et al., "Integration of Paper-based Microfluidic Devices with Commercial Electrochemical Readers," Lab on a Chip, 2010, 10, 3163-3169.

Palchetti, et al., "Characterisation of Screen-Printed Electrodes for Detection of Heavy Metals," Mikrochimica Acta, 1999, vol. 131, 65-73.

Palchetti, et al., "Electroanalytical biosensors and their potential for food pathogen and toxin detection," Anal. Bioanal. Chem., 2008, vol. 391, 455-471.

Park, et al, "Chemical methods for the production of graphenes," Nature Nanotechnology, 2009, vol. 4: 217-224.

Philips, et al., "Development of a novel cyano group containing electrochemically deposited polymer film for ultrasensitive simultaneous detection of a trace level cadmium and lead," Journal Hazardous Materials, 2012, 237-238, 46-54.

Plumlee, et al, "Linking Geological and Health Sciences to Assess Childhood Lead Poisoning from Artisanal Gold Mining in Nigeria," Environmental Health Perspectives, 2013, vol. 121, No. 6, 744-750.

Prats-Alfonso et al., "Iridium oxide pH sensor for biomedical applications. Case urea-urease in real urine samples," Biosensors and Bioelectronics 39: 163-169 (2013).

Prestel, et al, "Detection of heavy metals in water by fluorescence spectroscopy: On the way to a suitable sensor system," Fresenius Journal of Analytic Chemistry, 2000, 368, pp. 182-191.

Priyanka, et al, "Nanobioprobe mediated DNA aptamers for explosive detection," Chemical Communications, 2014, vol. 50: 1080-1082.

Pumera, "Graphene-based nanomaterials and their electrochemistry," Chemical Society Reviews, 2010, vol. 39: 4146-4157.

Rahman, et al, "Characterization of an EDTA Bonded Conducting Polymer Modified Electrode: Its Application for the Simultaneous Determination of Heavy Metal Ions," Analytic Chemistry, 2003, vol. 75: 1123-1129.

Raj, et al., "Fabrication of Electrochemically Reduced Graphene Oxide Films on Glassy Carbon Electrode by Self-Assembly Method and Their Electrocatalytic Application," The Journal of Physical Chemistry C, 2013, 117, 4326-4335.

Raj, et al., "Simultaneous determination of uric acid, xanthine, hypoxanthine and caffeine in human blood serum and urine samples using electrochemically reduced graphene oxide modified electrode," Analytica Chimica Acta, 2013, 771, 14-20.

Ramesha, "Electrochemical Reduction of Oriented Graphene Oxide Films: An in Situ Raman Spectroelectrochemical Study," Journal of Physical Chemistry C, 2009, 113, 7985-7989.

Rattanarata, et al., "Sodium dodecyl sulfate-modified electrochemical paper-based analytical device for determination of dopamine levels in biological samples," Analytica Chimica Acta, 2012, vol. 744, 1-7.

Salaun, et al., "Voltammetric Detection of Mercury and Copper in Seawater Using a Gold Microwire Electrode," Anal. Chem., 2006, vol. 78, 5052-5060.

Schiewe, et al, "Linear-Scan Anodic Stripping Voltammetry with Thin-Film Electrodes: Theory of the Stripping Stage and Experimental Tests," Analytical Chemistry, 1997, vol. 69, 2673-2681.

Service, "Carbon Sheets an Aton Thick Give Rise to Graphene Dreams," Science, 2009, vol. 324, 875-877.

Shen, et al, "Synthesis of graphene oxide-based biocomposites through diimide-activated amidation," Journal of Colloid Interface Science, 2011, vol. 356, 543-549.

Stankovich, et al, "Graphene-based composite materials," Nature, 2006, vol. 442: 282-286.

Suleiman, et al, Journal of Hazardous Materials, "Determination of Cd, Co, Ni and Pb in biological samples by microcolumn packed with bliack stone (Pierre noire) online coupled with ICP-OES," 2008, vol. 157, 410-417.

Sundramoorthy, et al., "Applications of Graphene in quality assurance and safety of food," Trends in Analytical Chemistry, 2014, vol. 60, 36-53.

Tan, "Paper Disk on Screen Printed Electrode for One-Step Sensing with an Internal Standard," Analytical Chemistry, 2010, vol. 82: 8844-8847.

Tian, et al, "Spectrochimica Acta Part A: Molecular and Biomolecular Spectroscopy," 2012, vol. 93, 335-342.

Tibbets, et al, "Sonoelectroanalytical detection of lead at a bare copper electrode," Fresenius' Journal of Analytical Chemistry, 2000, vol. 368: 412-414.

Tolani, et al., "Rapid and Efficient Removal of Heavy Metal Ions from Aqueous Media Using Cysteine-Modified Polymer Nanowires," Journal Applied Polymer Science, 2010, vol. 116, 308-313S.

US Environmental Protection Agency, "Update of Ambient Water Quality Criteria for Cadmium," 2001.

US Environmental Protection Agency, "Drinking Water Contaminants—Standards and Regulations," <http://water.epa.gov/drink/contaminants/basicinformation/lead.cfm.>, website available at least as early as May 22, 2017.

Wang, "L-Aspartic acid/L-cysteine/gold nanoparticle modified microelectrode for simultaneous detection of copper and lead,", Thin Solid Films 2012, 520, 6658-6663.

Wang, et al., "Bismuth/Polyaniline/Glassy Carbon Electrodes Prepared with Different Protocols for Stripping Voltammetric Determination of Trace Cd and Pb in Solutions Having Surfactants," Electroanalysis, 2010, vol. 22, No. 2, 209-215.

Wei, et al, "High adsorptive γ-AlOOH(boehmite)@SiO2/Fe3O4 porous magnetic microspheres for detection of toxic metal ions in drinking water," Chemical Communications, 2011, vol. 47: 11062-11064.

(56) References Cited

OTHER PUBLICATIONS

Wei, et al, "Selective detection toward Hg(II) and Pb(II) using polypyrrole/carbonaceous nanospheres modified screen-printed electrode," Electochimica Acta, 2013, vol. 105: 218-223.

Wei, et al, "Sn/O2/Reduced Graphene Oxide Nanocomposite for the Simultaneous Electrochemical Detection of Cadmium(II), Lead(II), Copper(II), and Mercury(II): An Interesting Favorable Mutual Interference," Physical Chemistry C, 2012, vol. 116, 1034-1041.

World Health Organization, "The world health report 2008," 2008, <http://www.who.int/whr/2008/en/index.html>.

World Health Organization, "Guidelines for Drinking-water Quality," 2011, <http://whqlibdoc.who.int/publications/2011/9789241548151eng.pdf.>.

Xu, et al., "Flexible Graphene Films via the Filtration of Water-Soluble Noncovalent Functionalized Graphene Sheets," Journal of the American Chemical Society, 2008, 130, 5856-5857.

Yamanaka, "The Electrochemical Behavior of Anodically Electrodeposited Iridium Oxide Films and the Reliability of Transmittance Variable Cells," Japanese Journal Applied Physics, 1991, 30, 1285-1289.

Yamanka, "Anodically Electrodeposited Iridium Oxide Films (AEIROF) from Alkaline Solutions for Electrochromic Display Devices," Japanese Journal of Applied Physics, 1989, 28, 632-637.

Yan, et al., "Fabrication of Free-Standing, Electrochemically Active, and Biocompatible Graphene Oxide-Polyaniline and Graphene-Polyaniline Hybrid Papers," ACS Applied Materials Interfaces 2010, vol. 2 No. 9, 2521-2529.

Yang, et al, "Paper-fluidic electrochemical biosensing platform with enzyme paper and enzumeless electrodes," Sensors and Actuators B: Chemical, 2014, 203:44-53.

Yang, et al, "Indium tin oxide-coated glass modified with reduced graphene oxide sheets and gold nanoparticles as disposable working electrodes for dopamine sensing in meat samples," Nanoscale, 2012, 4, 4594-4602.

Yang, et al, "Nickel nanoparticle-chitosan-reduced graphene oxide-modified screen-printed electrodes for enzyme-free glucose sensing in portable microfluidic devices," Biosensors Bioelectronics, 2013, 47, 530-538.

Yang, et al., "A highly sensitive non-enzymatic glucose sensor based on a simple two-step electrodeposition of cupric oxide (CuO) nanoparticles onto multi-walled carbon nanotube arrays," Talanta, 2010, vol. 82, 25-33.

Yang, et al., "Cyanobacterium metallothionein decorated graphene oxide nanosheets for highly selective adsorption of ultra-trace cadmium," Journal Materials Chemistry, 2012, 22, 21909-21916.

Yang, et al., "Electrochemical synthesis of reduced graphene sheet-AuPd alloy nanoparticle composites for enzymatic biosensing," Biosensors and Bioelectronics, 2011, 29, 159-166.

Yantasee, et al, "Voltammetric detection of lead (II) and mercury (II) using a carbon paste electrode modified with thiol self-assembled monolayer on mesoporous silica (SAMMS), " 2003, Analyst, vol. 128, pp. 467-472.

Yasri et al., "Highly selective mercury detection at partially oxidized graphene/poly(3,4-ethylenedioxythiophene):poly(styrenesulfonate) nanocomposite film-modified electrode," Frontiers in Materials, 2014, vol. 1, Article 33, pp. 1-10.

Ye, et al, "A novel nitrite sensor based on graphene/polypyrrole/chitosan nanocomposite modified glassy carbon electrode," 2011, Analyst, vol. 136, pp. 4563-4569.

Zhang, et al, "Graphene modified carbon nanosheets for electrochemical detection of Pb(II) in water," 2013, Journal of Materials Chemistry A, vol. 1, p. 13139-13145.

Zhao, "A microfluidic paper-based electrochemical biosensor array for multiplexed detection of metabolic biomarkers," 2013, Science and Technology of Advanced Materials vol. 14, Issue 5, 054402.

Zhu, et al, "Highly Sensitive Electrochemical Sensor for Mercury (II) Ions by Using a Mercury-Specific Oligonucleotide Probe and Gold Nanoparticle-Based Amplification," 2009, Analytical Chemistry, vol. 81, pp. 7660-7666.

Zhu, et al, "Simultaneous determination of Cd(II) and Pb(II) using square wave anodic stripping voltammetry at a gold nanoparticle-graphene-cysteine composite modified bismuth film electrode," 2014, Electrochimica Acta, vol. 115, pp. 471-477.

Zougagh, et al, "Automatic on line preconcentration and determination of lead in water by ICP-AES using a TS-microcolumn," Talanta, 2004, vol. 62, pp. 503-510.

European Patent Office Extended Search Report for Application No. 15865172.9 dated Nov. 14, 2018 (12 pages).

Chinese Patent Office Action for Application No. 201580075399.2 dated Jan. 31, 2019 (27 pages, English translation included).

Chinese Patent Office Action for Application No. 201580075399.2 dated Aug. 14, 2019 (22 pages, English translation included).

\* cited by examiner

CONTAMINANT DETECTION DEVICE AND METHOD

CROSS-REFERENCE TO RELATED APPLICATIONS

This application is a national stage filing under 35 U.S.C. 371 of International Application No. PCT/US2015/063809, filed Dec. 3, 2015, and claims priority to U.S. Provisional Patent Application No. 62/087,032 filed on Dec. 3, 2014, and to U.S. Provisional Patent Application No. 62/145,826 filed on Apr. 10, 2015, the entire contents of which are hereby incorporated by reference in their entireties.

STATEMENT REGARDING FEDERALLY-SPONSORED RESEARCH OR DEVELOPMENT

This invention was made with government support under 11-CRHF-0-6055 awarded by the USDA/NIFA and 0968887 awarded by the NSF. The government has certain rights in the invention.

FIELD OF THE INVENTION

The present invention relates to fluid testing, and more particularly to contaminant and pH level testing in fluid samples.

BACKGROUND OF THE INVENTION

Contamination of soil, ground water, and air with contaminants such as lead (Pb), mercury (Hg), cadmium (Cd), copper (Cu), zinc (Zn), etc. can present environmental and health issues. Even in trace concentrations, contaminants present in air, food, and drinking water can bio-accumulate and thus pose a threat to human health. This threat has led organizations to set guidelines for levels of concentration of certain containments. For example, the World Health Organization (WHO) has established a guideline limiting lead concentration in drinking water as 10 ppb. Still, according to the United States Environmental Protection Agency (USEPA), 10-20% of adults and 40-60% of infants are exposed to lead via drinking water.

SUMMARY OF THE INVENTION

With the aforementioned in mind, various embodiments of the invention provide improved methods and devices for detecting and monitoring the concentration of contaminants in fluid samples. Additionally, various embodiments of the invention provide improved methods and devices for measuring a pH level of a fluid sample, which has a variety of applications, one of which being a more precise determination of contaminant concentration in the fluid sample.

The present invention provides, in one aspect, a device for measuring the concentration of contaminants within a fluid sample. The device includes a power source, and a control unit electrically coupled to the power source. The control unit is configured to supply an input signal and measure a corresponding output signal from an electrode assembly. The electrode assembly includes a first contact electrically coupled to a reference electrode, a second contact electrically coupled to a cysteine functionalized graphene oxide with polypyrrole nanocomposite modified working electrode, and a third contact electrically coupled to a counter electrode. The output signal is indicative of contaminant concentration within the fluid sample.

The present invention provides, in another aspect, an electrode assembly for measuring the concentration of contaminants within a fluid sample. The electrode assembly includes a first contact electrically coupled to a reference electrode, a second contact electrically coupled to a cysteine functionalized graphene oxide with polypyrrole modified working electrode, and a third contact electrically coupled to a counter electrode.

The present invention provides, in yet another aspect, a method for measuring contaminant concentration within a fluid sample using a contaminant detection device that includes an electrode assembly and a control unit. First, a fluid sample is placed into contact with the electrode assembly that includes a reference electrode, a measurement electrode having a cysteine functionalized graphene oxide with polypyrrole nanocomposite, and a counter electrode. The control unit then applies a first electrical signal to the measurement electrode, and subsequently applies a second electrical signal to the measurement electrode. The control unit is configured to measure an output signal across the counter electrode and the measurement electrode with the control unit while applying the second electrical signal in order to determine a contaminant concentration based on the output signal.

The present invention provides, in yet another aspect, a method for measuring contaminant concentration within a fluid sample using a contaminant detection device that includes an electrode assembly and a control unit. First, a fluid sample is placed into contact with the electrode assembly that includes a reference electrode, a measurement electrode, and a counter electrode. The control unit then measures a circuit potential of the electrode assembly in order to determine a pH of the fluid sample either before, after, or while applying a first electrical signal to the measurement electrode. The method also includes the control unit applying a second electrical signal to the measurement electrode and measuring a change in potential across the measurement electrode and the counter electrode. The method further includes the control unit correlating the first output to a contaminant concentration within the fluid sample based on the pH of the fluid sample.

The present invention provides, in yet another aspect, a device for measuring the concentration of contaminants within a fluid sample. The device includes a power source and a control unit electrically coupled to the power source. The control unit is configured to supply a first input signal and a second input signal to, and measure a corresponding first output signal and second output signal from, an electrode assembly that includes a first contact electrically coupled to a reference electrode, a second contact electrically coupled to measurement electrode, and a third contact electrically coupled to a counter electrode. The first output signal is indicative of a pH of the fluid sample, and the second output signal is correlated to a contaminant concentration within the fluid sample based on the pH of the fluid sample.

The present invention provides, in yet another aspect, a device for measuring the pH of a fluid sample. The device includes a power source and a control unit electrically coupled to the power source. The control unit is configured to measure an output signal from an electrode assembly that includes a first contact electrically coupled to a reference electrode, and a second contact electrically coupled to a working electrode including a graphene oxide layer and a metal oxide layer. The device also includes a microfluidic paper filter configured to receive the fluid sample and deliver the fluid sample to the electrode assembly. The output signal measured by the control unit is indicative of a pH level within the fluid sample.

The present invention provides, in yet another aspect, a method for measuring pH within a fluid sample using a pH detection device including a microfluidic filter paper, an electrode assembly and a control unit. First, a fluid sample is placed into contact with the microfluidic filter paper, which transports the fluid sample via capillary action within the microfluidic filter paper to the electrode assembly. The electrode assembly includes a reference electrode and a working electrode having a graphene oxide layer and a metal oxide layer. The control unit is configured to measure a circuit potential of the electrode assembly and fluid sample to determine a pH of the fluid sample based on the circuit potential.

Other features and aspects of the invention will become apparent by consideration of the following detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., instructions stored on non-transitory computer-readable medium) executable by one or more processing units, such as a microprocessor and/or application specific integrated circuits ("ASICs"). As such, it should be noted that a plurality of hardware and software based devices, as well as a plurality of different structural components may be utilized to implement the invention. For example, "servers" and "computing devices" described in the specification can include one or more processing units, one or more computer-readable medium modules, one or more input/output interfaces, and various connections (e.g., a system bus) connecting the components.

DETAILED DESCRIPTION

Figure 1A:
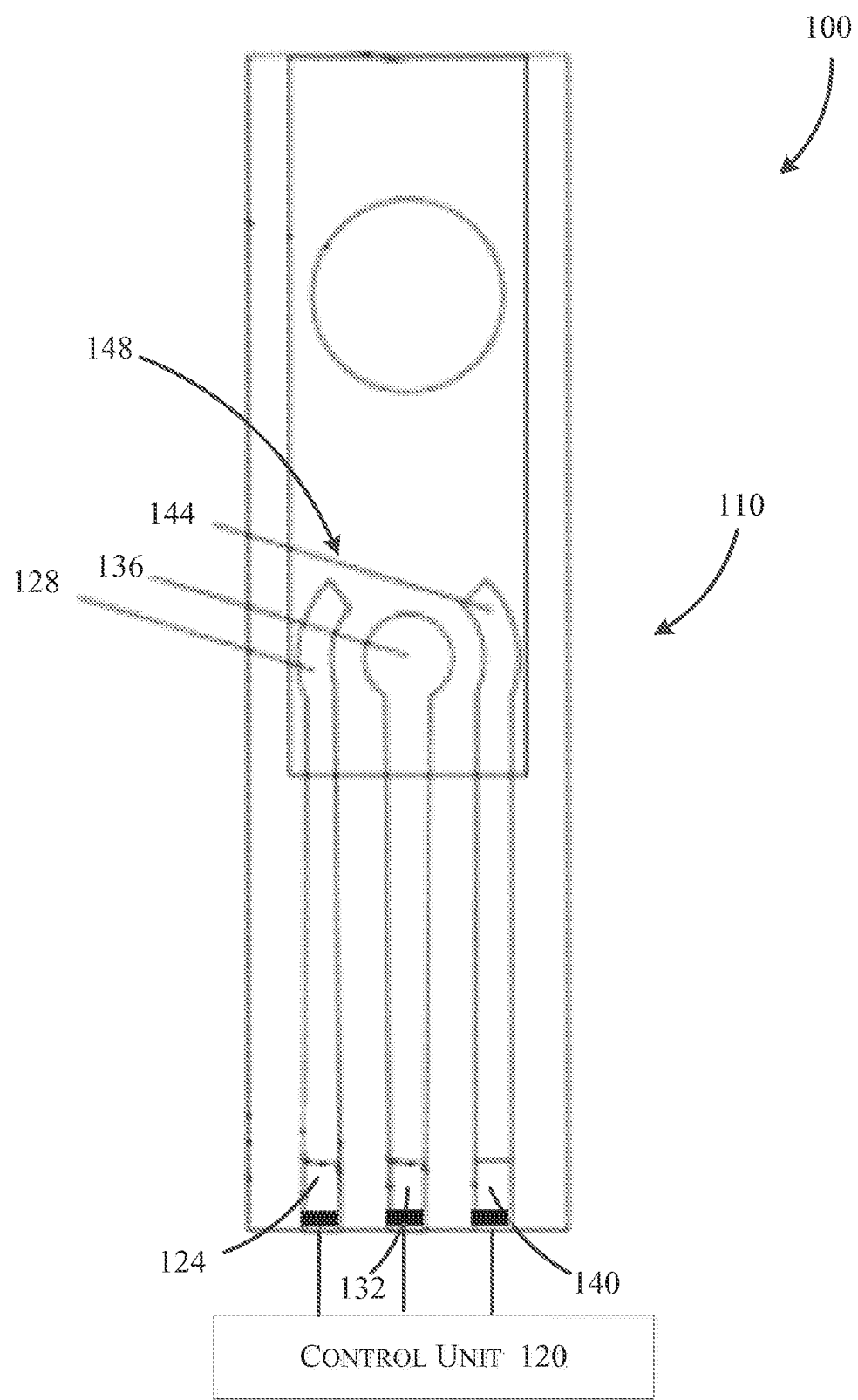
FIG. 1A is a schematic of a contaminant detection device.
Figure 1B:
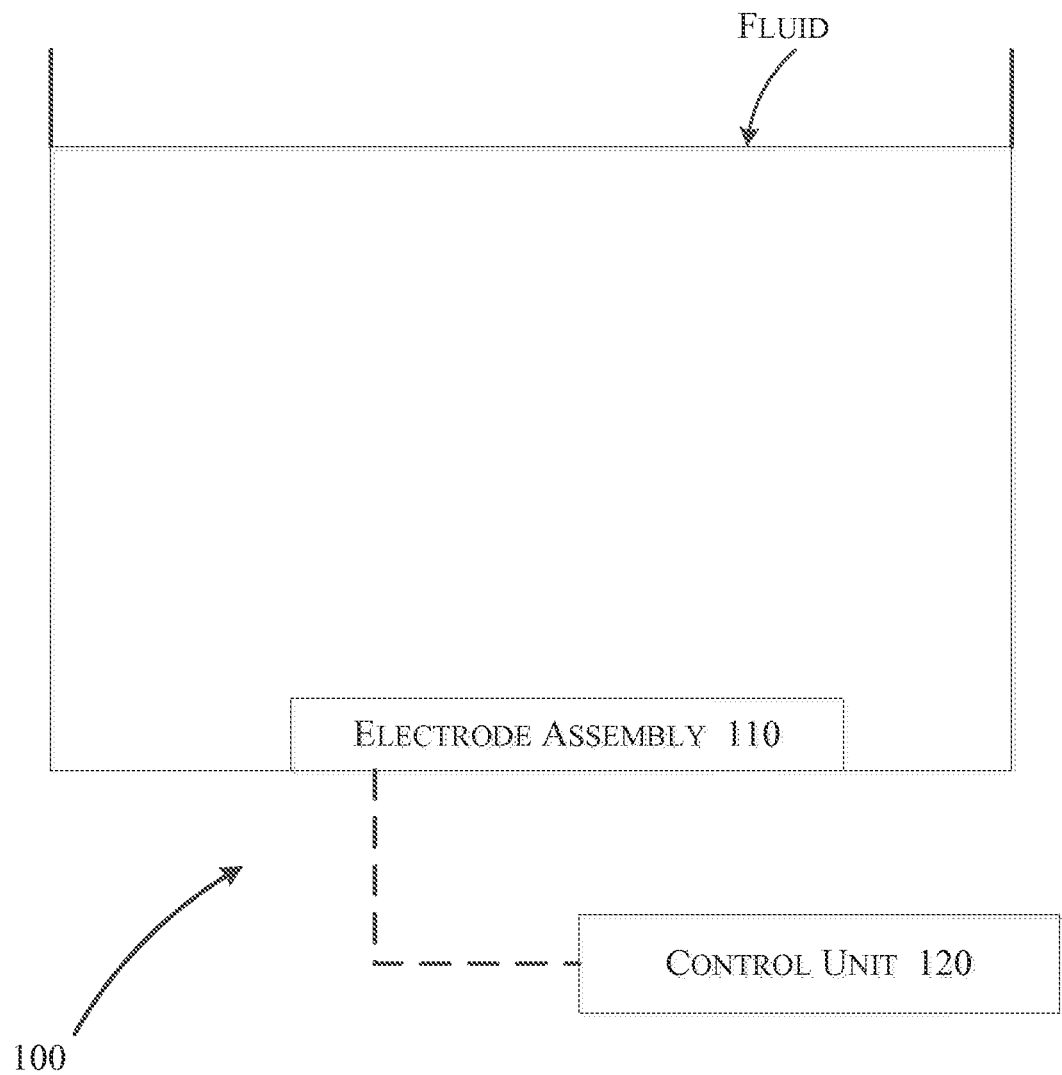
FIG. 1B is a schematic of an exemplary use of the contaminant detection device of FIG. 1A.
Figure 10A:
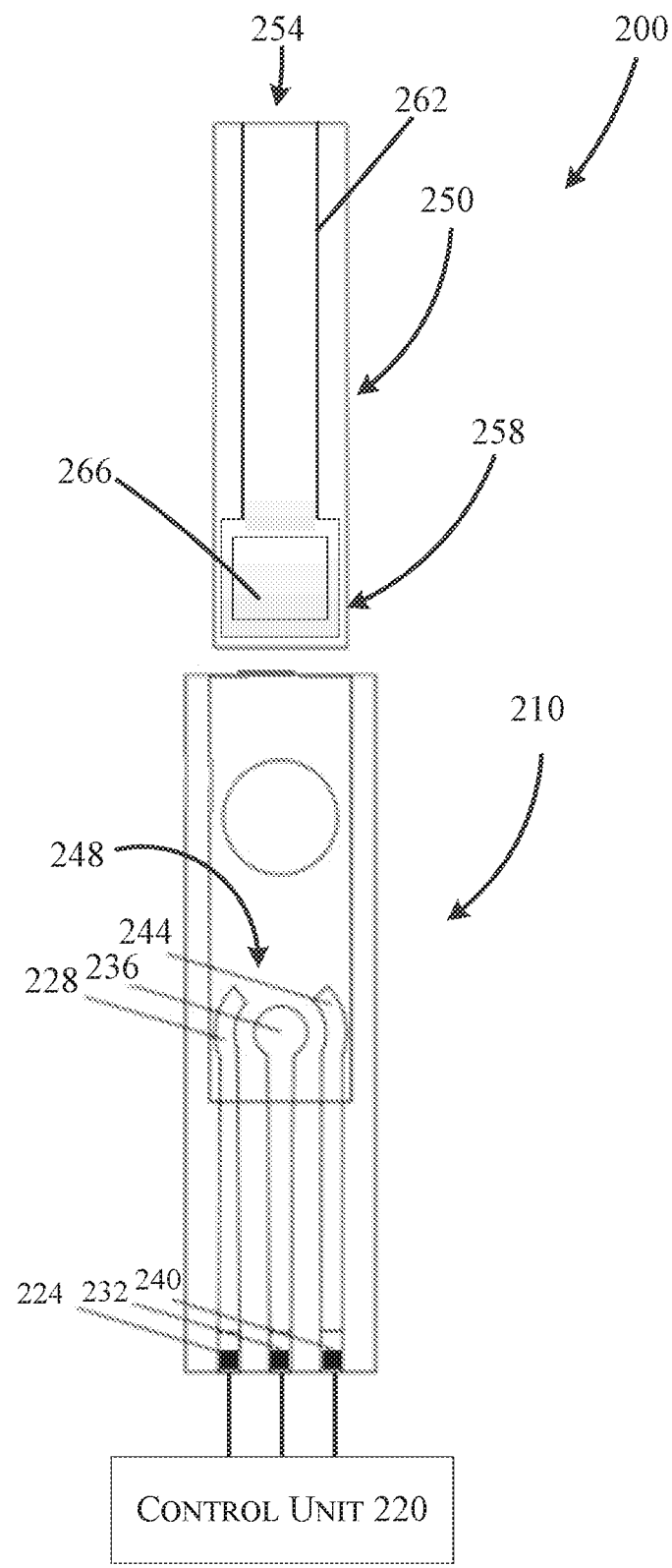
FIG. 10A is a schematic view of a contaminant detection device according to another embodiment of the invention.
Figure 10B:
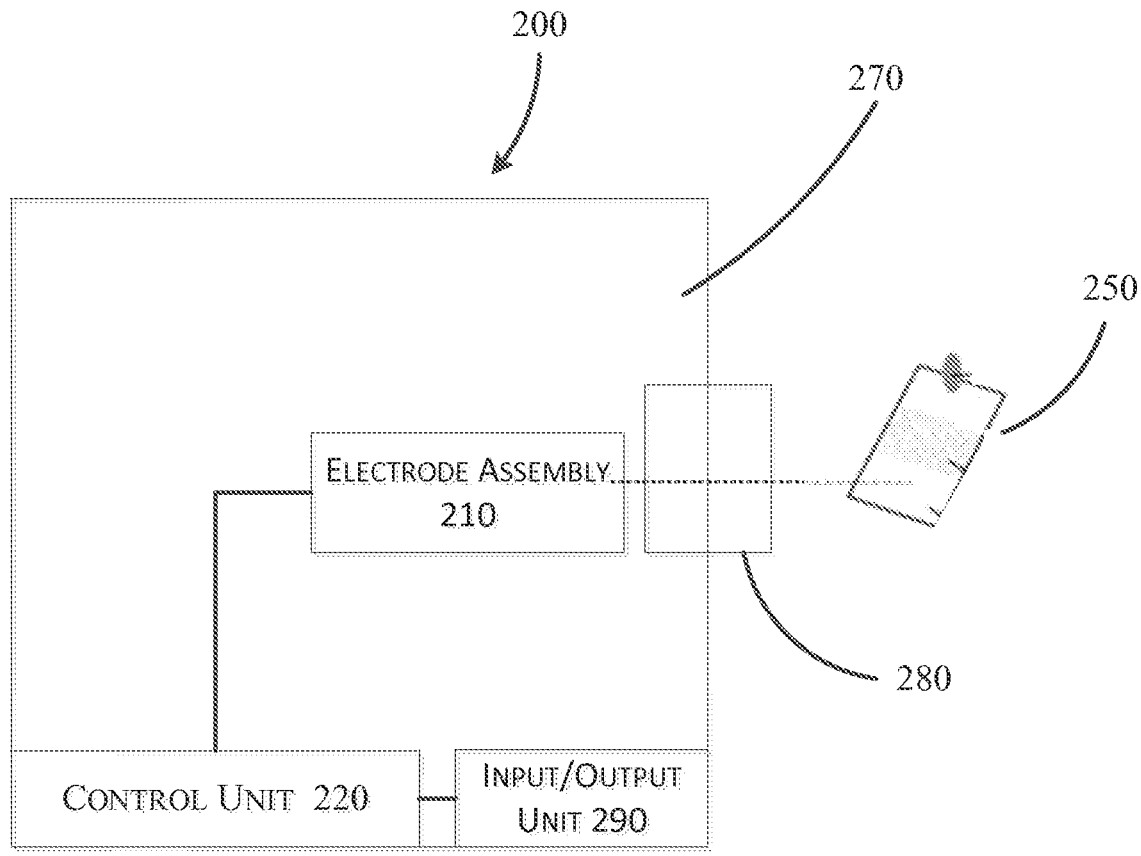
FIG. 10B is a plan view of the contaminant detection device of FIG. 10A.

FIGS. 1A-1B and 10A-10B illustrate two detection devices 100, 200 including an electrode assembly 110 that is electrically coupled to a control unit 120. The detection devices 100, 200 may be configured to detect the concentration of contaminants such as arsenic, lead, copper, cadmium, mercury, chromium, zinc, barium, bromine, and fluoride, among others, in a fluid sample. In addition, the detection devices 100, 200 can separately or simultaneously measure the pH of the fluid sample. As seen in FIGS. 1B and 10B, respectively, the detection devices 100, 200 may be fully immersed in a fluid sample to continuously monitor contaminant concentration and pH levels (e.g., placed directly into a water supply such as a pipe or reservoir), or alternately the devices 100, 200 may be a handheld, portable, and at least partially reusable device for spot testing fluid samples. Such a handheld device includes a graphical user interface (GUI) such that pH level and contaminant concentration may be displayed to the user. A handheld device is a device that, generally speaking, can be held, maneuvered, positioned, and operated using one or two hands of a typical user, which is in contrast to a device having a size and/or weight that prohibits a typical user from holding, maneuvering, positioning, and/or operating the device by hand without the assistance of additional users and/or supporting equipment (e.g., carts, tables, lifts, vehicles, etc.).

FIG. 1A illustrates a first exemplary embodiment of the detection device 100 configured to detect contaminants and pH of a fluid sample. The electrode assembly 110 includes a first contact 124 coupled to a reference electrode 128, a second contact 132 coupled to a working electrode 136, and a third contact 140 coupled to a counter electrode 144. Collectively, the reference electrode 128, the working electrode 136, and the counter electrode 144 define a working area 148 configured to receive the fluid sample.

In one construction, the electrode assembly 110 is a screen printed electrode assembly 110 having the reference electrode 128 and the counter electrode 144 constructed from a first material or combination of materials (e.g., silver/silver chloride (Ag/AgCl), graphite/AgCl, standard hydrogen, silver/silver iodide (Ag/AgI), iridium oxide ($IrO_2$), etc.) and a working electrode 136 constructed with a cysteine functionalized graphene oxide with polypyrrole nanocomposite. As will be described in detail below, the cysteine functionalized graphene oxide with polypyrrole nanocomposite advantageously increases the sensitivity to contaminant ions thereby improving overall performance of the device 100. However, other constructions of working electrodes 136, such as electrochemically reduced graphene oxide (ErGO)/poly(diallyldimethylammonium chloride) (PDDA)-Tris(2-carboxyethyl)phosphine (TCEP), ErGO/PDDA/TCEP coated gold nanoparticles (AuNPs), or cystamine-chitosan/ErGO are used in other embodiments.

Each of the first contact 124, the second contact 132, and the third contact 140 are electrically coupled to the control unit 120. The control unit 120 is a microprocessor, application specific integrated circuit (ASIC), digital signal processor, or another computer processing unit, which may be integrally supported within a device housing or alternatively may form at least part of a peripheral computing device. The control unit 120 may be configured to apply and measure a variety of signals to and from the electrode assembly 110 in order to measure contaminant concentration and pH. For example, in some embodiments, the control unit 120 includes a processing unit in communication with a memory (e.g., read only memory (ROM), random access memory (RAM), or flash memory) storing instructions and data. The processing unit executes instructions read from the memory to carry out the functionality of the control unit 120 described herein. Further, the results of measurements and calculations of the control unit 120 (e.g., containment and pH levels) are stored in the memory thereof and may be displayed on a display screen coupled to the control unit 120 and/or exported to another computing device (e.g., a laptop, tablet, mobile device, personal computer, or server) either directly or via one or more networks (e.g., local area networks and/or wide area networks).

As explained in further detail below, in one construction, the control unit 120 is configured to measure electrical signals, such as a current, across the working electrode 136, the working area 148, and the counter electrode 144 via the second contact 132 and the third contact 140. In addition, the control unit 120 is configured to apply a complex signal 126 to the working electrode 136 via the second contact 132. This combination of signaling and measuring allows the control unit 120 to perform voltammetry to identify and quantify contaminant ions in the fluid sample. In one embodiment, the voltammetry operation is anodic stripping voltammetry. However, various other voltammetry operations, such as cathodic stripping voltammetry, adsorptive stripping voltammetry, and others are used in some embodiments.

Figure 2:
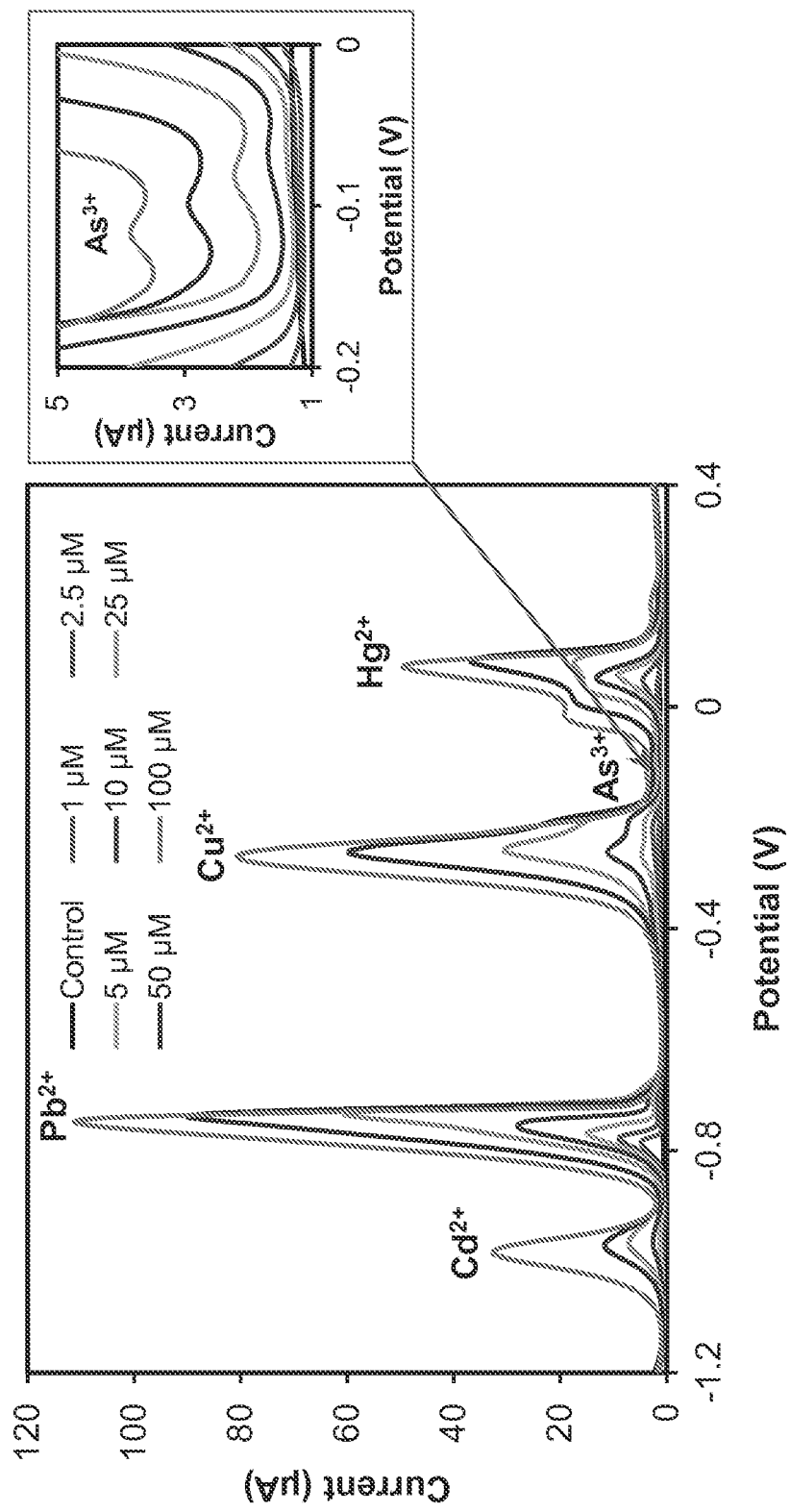
FIG. 2 is a graph of potential vs. current for contaminant ion detection using the contaminant detection device of FIG. 1A.

In operation, to identify contaminant ions within a fluid sample, the fluid sample is first received within the working area 148 via direct application by a user (e.g., using a pipette, etc.) or from constant contact with a fluid sample when the device 100 is completely immersed in a fluid (FIG. 1B), for example. Then, the control unit 120 applies the complex signal 126 to the working electrode 136 via the second contact 132 while current is measured across the working electrode 136 and the counter electrode 144. The complex signal 126 is a sequence of voltages applied to the working electrode 136 in a specific order (example described below) such that contaminant ion species within the fluid sample are accumulated or deposited on (i.e., electrochemically bonded to), and subsequently stripped from, the surface of the working electrode 136. During application of the sequence of voltages, the monitored current will vary due to the stripping of each contaminant ion species from the surface of the working electrode 136 at characteristic voltages for each contaminant ion species. The control unit 120 can thereby determine the concentration of each contaminant ion species within the fluid sample by correlating the measured current at the characteristic voltage to the concentration of the contaminant ion species. For example, as shown in FIG. 2, the control unit 120 may correlate the current measured across the working electrode 136 and the counter electrode 144 (y-axis) at specific voltages of the complex signal 126 (x-axis) to determine a concentration of various contaminant ions within the fluid sample. As illustrated in FIG. 2, larger measured currents at voltage values of the complex signal 126 associated with specific contaminant ions indicates a higher concentration of that contaminant ion species within the fluid sample.

Figure 3:
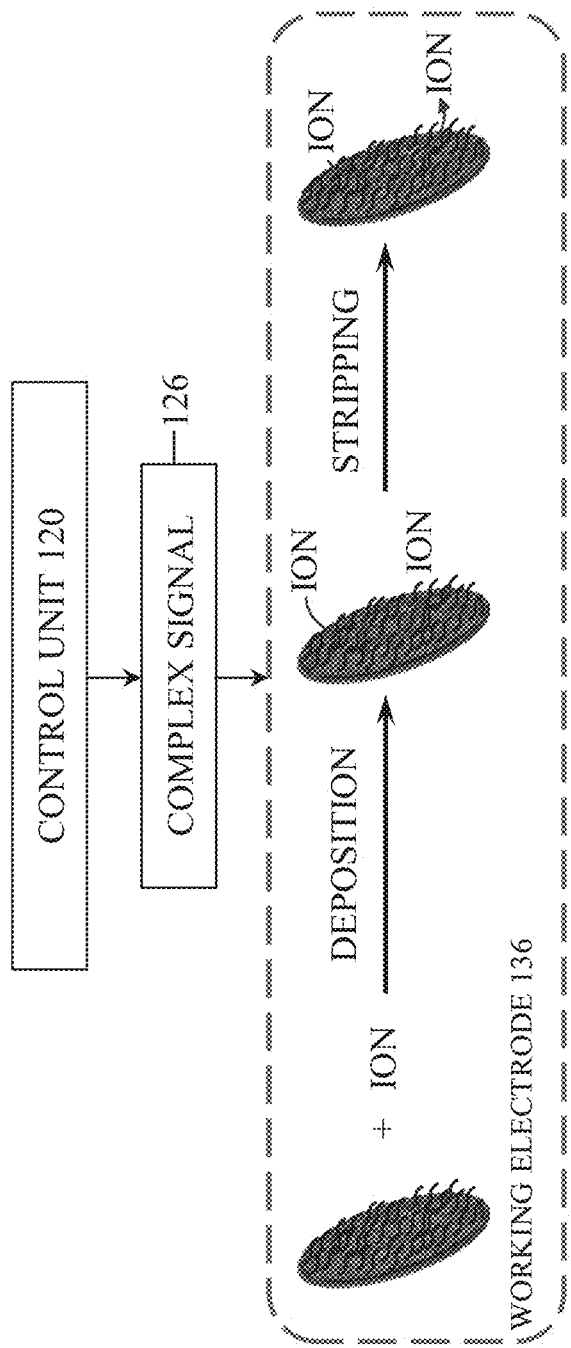
FIG. 3 is a flow chart illustrating the operation of the detection device of FIG. 1A using anodic stripping voltammetry

In a specific example using differential pulse anodic stripping voltammetry, illustrated in FIG. 3, the complex signal 126 involves a deposition or reduction potential that is applied by the control unit 120 to the working electrode 136 in an open circuit condition. The deposition potential voltage level and the time period for which it is applied may vary depending on particulars of a sample or containments to be measured. In some embodiments, for example, the deposition potential is between approximately −1.6V and −1.0V that is applied for between 8 and 15 minutes. In one embodiment, the deposition potential is approximately −1.2V and is applied for 10 minutes. By applying the deposition potential for a desired time period, contaminant ions within the fluid sample are deposited on the working electrode 136. Subsequently, the control unit 120 scans the complex signal 126 in a differential pulse waveform from the deposition potential to a stripping or oxidizing potential of between about −1.6V to +0.4V in order to strip the contaminant ions from the working electrode 136. The differential pulse waveform can utilize varied parameters to scan the complex signal 126 between the deposition potential and the oxidizing potential. For example, the applied deposition potential may be 1.2 V applied for 10 minutes, and the stripping or oxidizing potential may be scanned from −1.2V to +0.2V. It should be noted that the scanning parameters may vary, and the scanning may also be done in a variety of other signal patterns. For example, the signal pattern may include a linear voltage sweep, a square wave, or other suitable signal patterns.

The pH of the fluid sample may also be determined during operation. This may be accomplished before, during, or after the identification of contaminant ions. To measure the pH of the fluid sample, the fluid sample is received in the working area 148. Then, the control unit 120 measures an open circuit potential between the working electrode 136 and the counter electrode 144. The resulting open circuit potential is proportional to the H±ion concentration of the fluid sample (i.e., the pH) such that the control unit 120 can determine the pH based on the measured open circuit potential.

Figure 4:
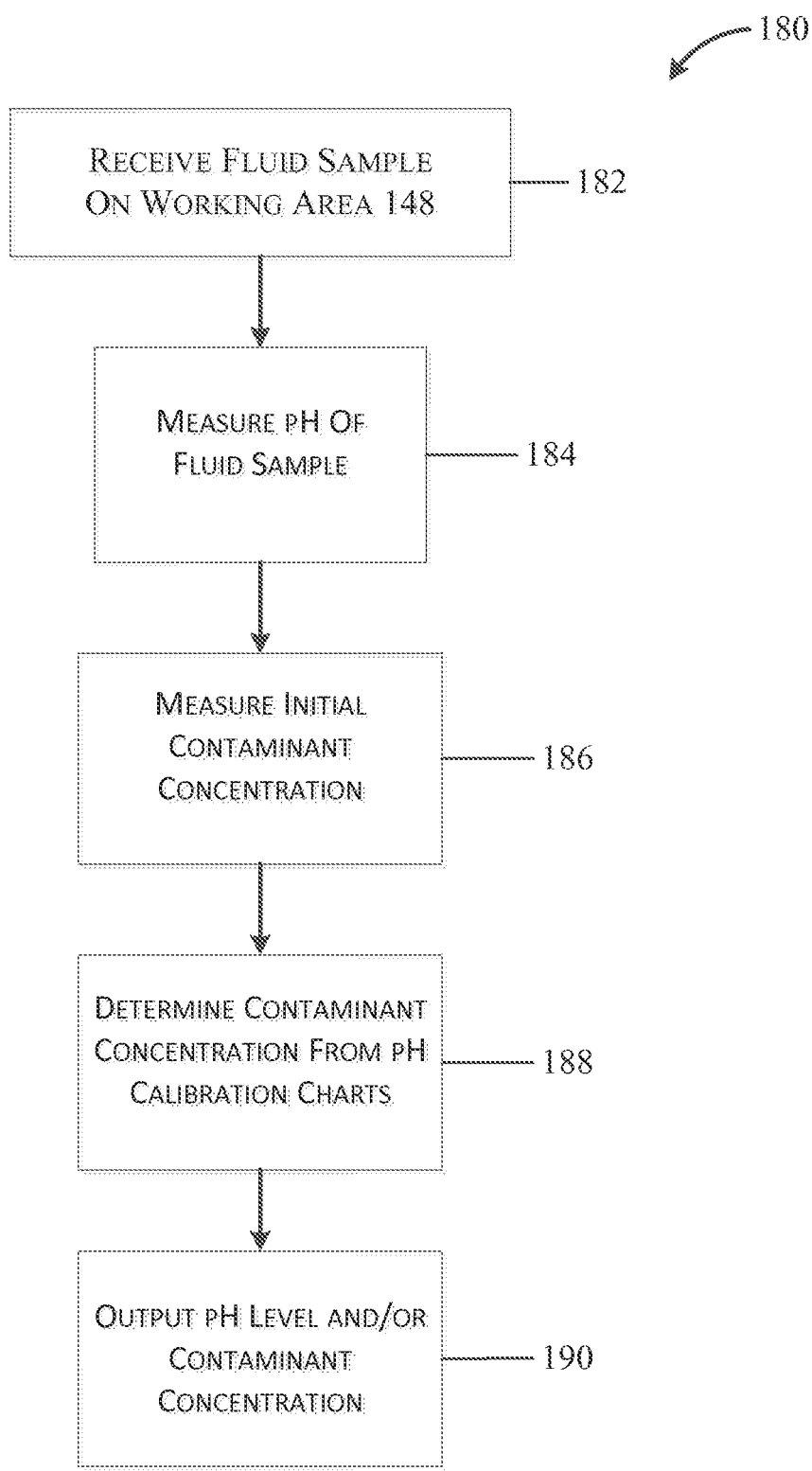
FIG. 4 is a flow chart illustrating a method for detecting contaminant ions and measuring pH levels using the contaminant detection device.

In one embodiment, illustrated the FIG. 4, the device 100 may be configured to calibrate the measurement of contaminant ion concentrations based on the measured pH of a fluid sample using a process 180. The process 180 includes a first step 182 where the device 100 receives a fluid sample on the working area 148. In a second step 184, the device 100 measures the pH of the fluid sample in the operation described above. Then, in a third step 186, which may occur before, during, or after the second step 184, the device 100 measures an initial contaminant concentration using the operation described above. Subsequently, in a fourth step 188, the control unit 120 uses the pH measurement to determine the contaminant concentration based on pH calibration charts. The pH calibration charts, which may be stored in a memory of the control unit 120, correlate the initial measured contaminant concentration to corrected contaminant concentrations values based on the measured pH of the fluid sample. Finally, in a fifth step 190, the device outputs a pH level and/or contaminant concentration to the user.

As noted above, the working electrode 136 is a cysteine functionalized graphene oxide with polypyrrole nanocomposite modified working electrode 136 in some embodiments. The cysteine functionalized graphene oxide with polypyrrole nanocomposite offers various advantages due to both individual material properties and synergistic effects. The incorporation of graphene enhances the performance of the electrochemical sensors. In particular, graphene offers advantages such as large specific surface area, flexibility, chemical stability, high conductivity, good nanocomposite forming ability, and enhanced electrocatalytic activity. Graphene oxide also affords easy surface modification via covalent grafting due to a large number of carboxyl, hydroxyl, and epoxide groups on its edge and basal plane.

Furthermore, cysteine has been found to have a high chelation capacity, which enhances accumulation of target metal ions on the electrode thereby enhancing contaminant detection in a fluid sample. Cysteine also binds particularly well with contaminant ions (e.g., heavy metals such as lead) through cooperative metal-ligand interaction.

Finally, the graphene and polypyrrole nanocomposite affords large surface area, fast electron transfer rate, increased mass-transport rate, enhanced electrocatalytic properties, lower solution resistance, and higher signal to noise ratio.

When taken also a whole, the cysteine functionalized graphene oxide with polypyrrole nanocomposite offers the advantages of various material components, such as high chelation capacity and a microporous layered structure of cysteine, and good conductivity of polypyrrole to achieve a highly sensitive contaminant detection device. A working electrode incorporating these materials is also functional at a variety of temperatures and pH values for the fluid sample, making the electrode more flexible in operation than electrodes in the prior art. In addition, the working electrode is stable for extended periods of time (e.g., months).

Examples of the use and advantages of the cysteine functionalized graphene oxide with polypyrrole nanocomposite modified working electrode 136 in device 100 are described below with respect to FIGS. 5A-5B.

Figure 5B:
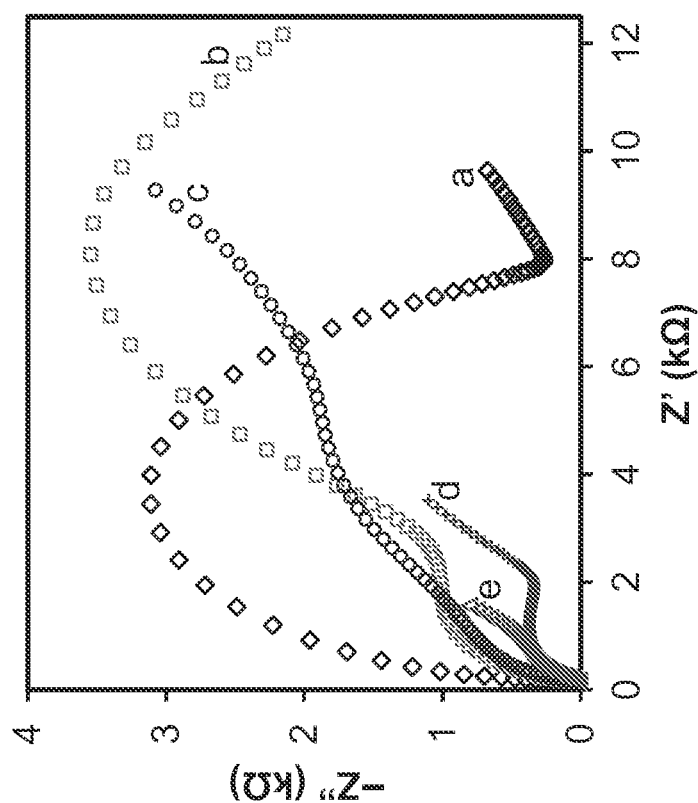
FIG. 5B illustrates electrochemical impedance spectroscopy of (a) a graphene oxide (GO-) modified working electrode, (c) a cysteine functionalized graphene oxide (sGO-) modified working electrode, (d) a polypyrrole (PPy-) modified working electrode, and (e) a cysteine functionalized graphene oxide with polypyrrole nanocomposite (sGO/PPy-) modified working electrode in 5 mM [Fe(CN)$_6$]$^{3/4}$ and 0.1 M KCl.
Figure 5A:
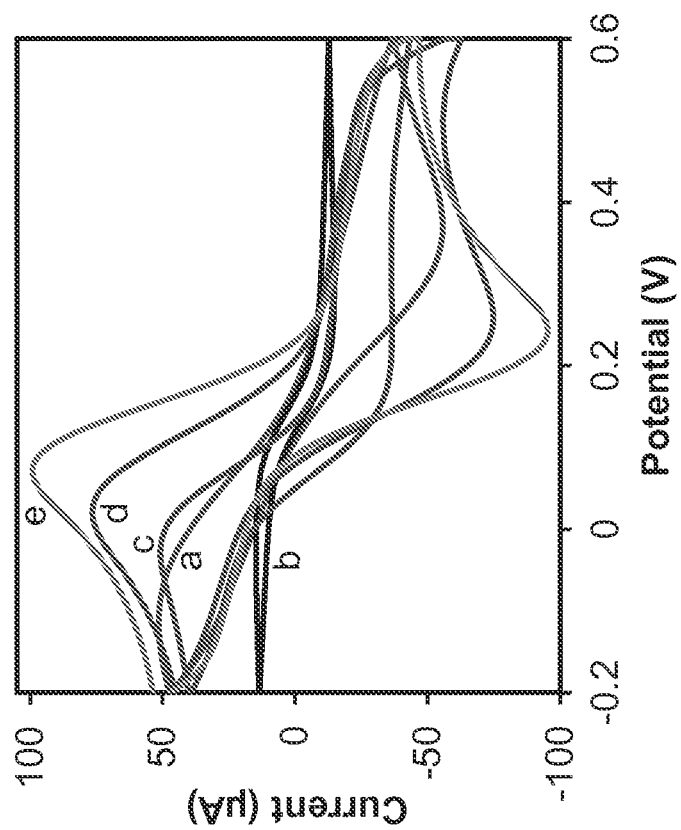
FIG. 5A illustrates typical cyclic voltammograms of (a) a bare (e.g., unmodified) working electrode and (b) a graphene oxide (GO-) modified working electrode, (c) a cysteine functionalized graphene oxide (sGO-) modified working electrode, (d) a polypyrrole (PPy) modified working electrode, and (e) a cysteine functionalized graphene oxide with polypyrrole nanocomposite (sGO/PPy) modified working electrode in 5 mM[Fe(CN)$_6$]$^{3-/4-}$ and 0.1 M KCl at scan rate of 50 mV/s.

FIG. 5A illustrates typical cyclic voltammetry responses of a bare (e.g., unmodified) working electrode and (b) a graphene oxide (GO-) modified working electrode, (c) a cysteine functionalized graphene oxide (sGO-) modified working electrode, (d) a polypyrrole (PPy-) modified working electrode, and (e) a cysteine functionalized graphene oxide with polypyrrole nanocomposite (sGO/PPy-) modified working electrode in 5 mM of redox couple $[Fe(CN)_6]^{3-/4-}$ and 0.1 M KCl solution. In FIG. 5A, curve 'a' shows quasi-reversible anodic and cathodic peaks of $[Fe(CN)_6]^{3-/4-}$ at the bare (i.e., unmodified) working electrode surface. The current at GO-modified working electrode (FIG. 5A, curve 'b') decreased more rapidly than bare (i.e., unmodified) working electrode. FIG. 5A also shows that curve 'c' exhibits a well-defined redox peak with increases in current at the sGO-modified working electrode. In the case of electrochemically polymerized PPy-modified working electrode (FIG. 5A, curve 'd'), well-defined reversible redox peaks were observed with up to two-fold increase in current than in the sGO-modified working electrode. This result confirms that PPy has good electron tunneling properties and enhances the rate of electron transfer at the electrode surface. Also in FIG. 5A, curve 'e' shows a further increase in current for the sGO/PPy-modified working electrode. The sGO/PPy-modified working electrode has a good Faradaic redox behavior compared with bare and PPy-, sGO-, and GO-modified SPEs. These results reveal that the sGO/PPy provides good conductivity, large surface area, and better electrochemical catalytic behavior, which promote electron transfer rate at the modified electrode surface and improve the sensitivity of lead sensing.

Electrochemical impedance spectroscopy measurements were performed to further investigate the electrode surface characteristics (FIG. 5B). In typical Nyquist plots of the EIS spectra, the diameter of semicircle parts at higher frequency range corresponds to electron-transfer-limiting process, and the linear parts at lower frequency range represent diffusion-limiting process. Thus, a large semicircle obtained at high frequency range (FIG. 5B, curve 'a') explains the poor electron transfer reaction of $[Fe(CN)_6]^{3/4}$ at the bare (i.e., unmodified) working electrode. For the GO-modified working electrode (FIG. 5B, curve 'b'), the charge transfer resistance ($R_{CT}$) value further increased up to 12.17 kΩ compared with that of bare SPE (7.97 kΩ). However, the sGO-modified working electrode shows two small semicircles with $R_{CT}$ values of 1.56 and 5.2 kΩ (FIG. 5B, curve 'c'). With the PPy-modified working electrode, the $R_{CT}$ value further decreased to 1.98 kΩ (FIG. 5B, curve 'd'), confirming the ability of PPy to promote electron-transfer reaction of $[Fe(CN)_6]^{3-/4-}$. With the sGO/PPy-modified working electrode, $R_{CT}$ (0.763 kΩ) decreased even more substantially as noted from the semicircle parts in the Nyquist plots being reduced to almost a straight line (FIG. 5B, curve 'e'). These EIS results concur with those obtained with cyclic voltammetry.

Figure 6B:
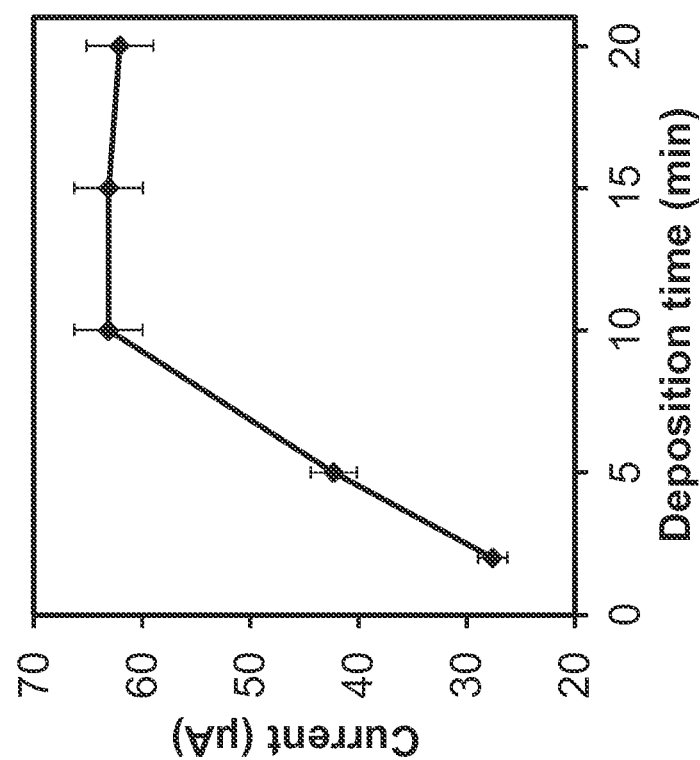
FIG. 6B is a graph of deposition time vs. current illustrating the relationship between the deposition time and measured current during use of the device of FIG. 1A.
Figure 6A:
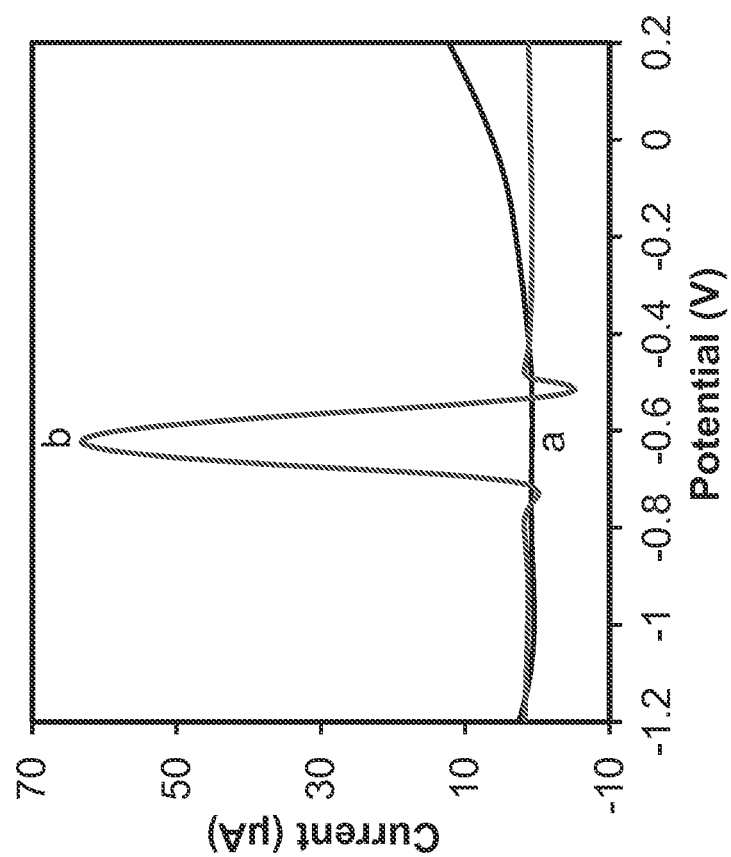
FIG. 6A is a graph of potential vs. current illustrating use of the device of FIG. 1A to measure (a) a fluid sample having no contaminant ions and (b) a fluid sample containing contaminant ions.

FIG. 6A-6B illustrate exemplary differential pulse anodic stripping voltammetry measurements taken by the device 100 having the cysteine functionalized graphene oxide with polypyrrole nanocomposite modified working electrode 136 for the detection of lead in a fluid sample (e.g., a 0.1 M sodium acetate-acetic acid (acetate) buffer at pH 5.0). The fluid sample was placed on the working area 148 and the complex signal 126 was applied according to the following exemplary parameters: first, a deposition potential of −1.2 V was applied for 10 min in open circuit condition, and then the signal was scanned from −1.2 to +0.2 V with an increment potential of 4 mV with a pulse amplitude of 50 mV, pulse width of 0.2 s and pulse period of 0.3 s. A well-defined stripping peak of lead is seen at approximately −0.63 V in FIG. 6A with an increase in current. With reference to FIG. 6B, the effect of deposition time at the exemplary deposition potential of −1.2 V presented with reference to FIG. 6A on the stripping peaks of lead is illustrated. The deposition time and potential used are merely exemplary, as time and potential values of higher or lower levels are used in some embodiments.

Figure 7:
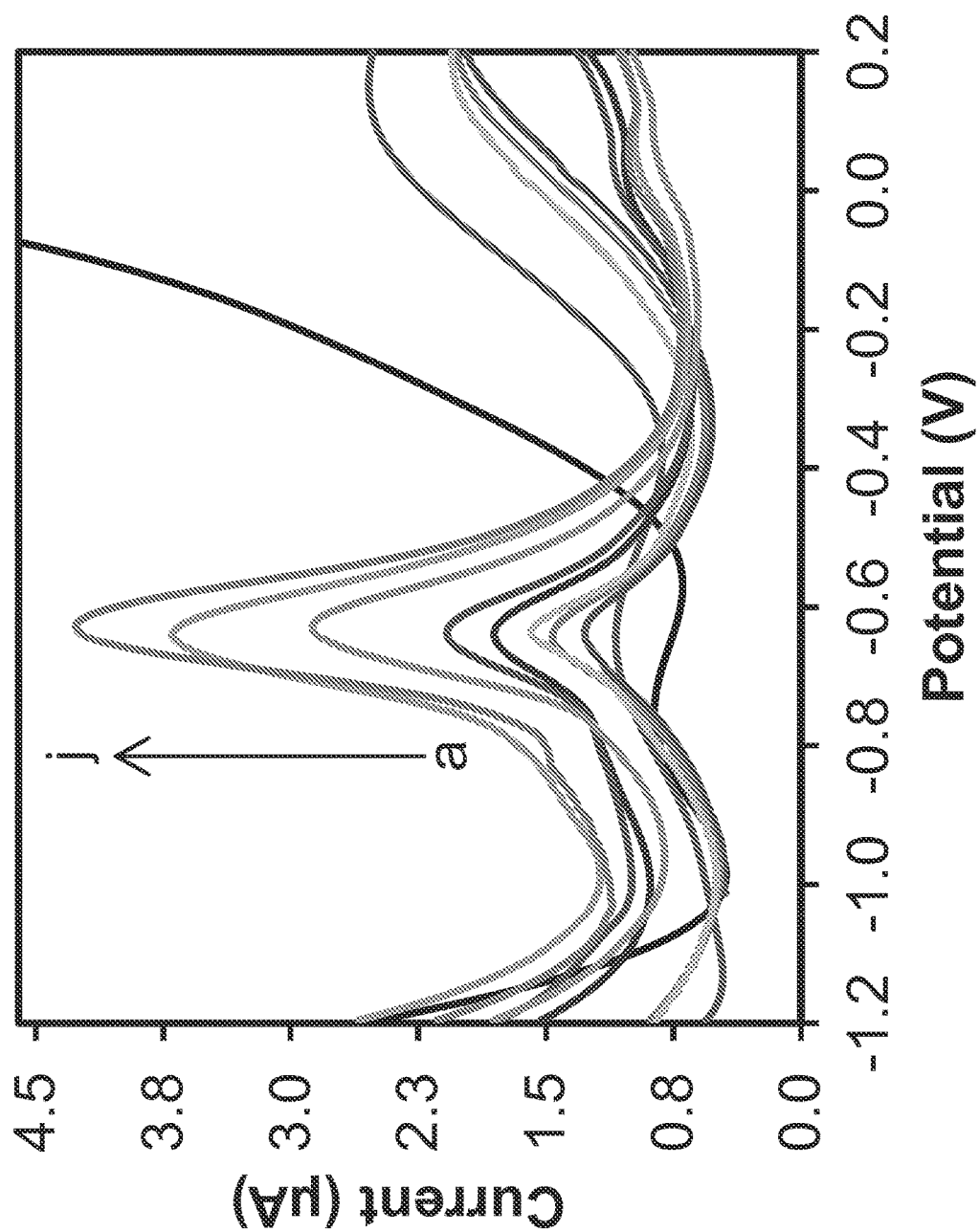
FIG. 7 illustrates potential vs. current measured for measurements taken with the device of FIG. 1A in fluid samples having varying contaminant ion concentrations.

FIG. 7 illustrates an exemplary set of differential pulse anodic stripping voltammetry measurements taken by the device 100 having the cysteine functionalized graphene oxide with polypyrrole nanocomposite modified working electrode 136 for the detection of various lead concentrations. The fluid samples had lead concentrations varying from 0.28 to 280 ppb. Well-defined stripping peaks, with peak currents increasing in proportion to the concentration of lead, were observed at −0.63 V.

Figure 8:
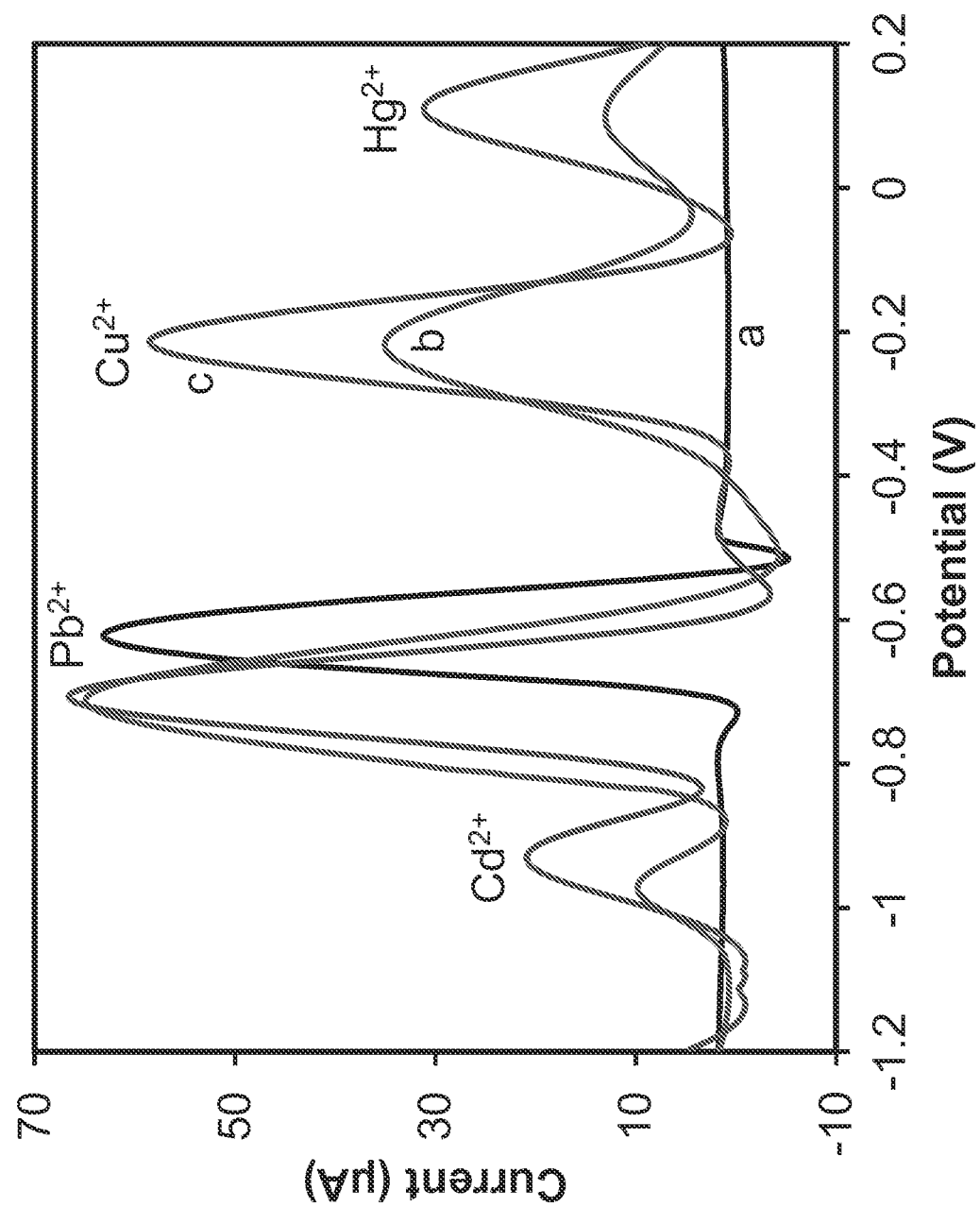
FIG. 8 is a graph of potential vs. current for measurements taken with the device of FIG. 1A in the absence (a) and in the presence (b) of 0.15 ppm of $Cd^{2+}$, 0.2 ppm of $Cu^{2+}$ and 0.3 ppm of $Hg^{2+}$, and (c) 14 ppm of $Cd^{2+}$, $Cu^{2+}$ and $Hg^{2+}$ each.

The selective detection of the sensor was investigated by introducing other contaminant ions (e.g., sodium, potassium, silver, cadmium, copper, mercury, calcium, magnesium, iron, cobalt, nickel, zinc, barium, etc.) individually along with lead and measuring the stripping peak potential at −0.63 V. The results show that the selective detection of lead or other contaminant ions using the cysteine functionalized graphene oxide with polypyrrole nanocomposite modified working electrode 136 was unaffected by the presence of these interfering contaminant ions. FIG. 8 shows the results. The peak current for lead changed only minimally (e.g., from 63.1 µA (without interferents) to 64.9 µA and 66.6 µA, with low and high concentrations of interferents, respectively), with the peak potential shifting slightly (e.g., from −0.63 V to −0.71 V). This marginal change in the signal may be attributed to the formation of intermetallic compounds (Pb—Hg, Pb—Cu) during the deposition step. However, the signal for lead is much different from those for interfering metals; hence, selective detection of lead is unaffected.

Figure 9:
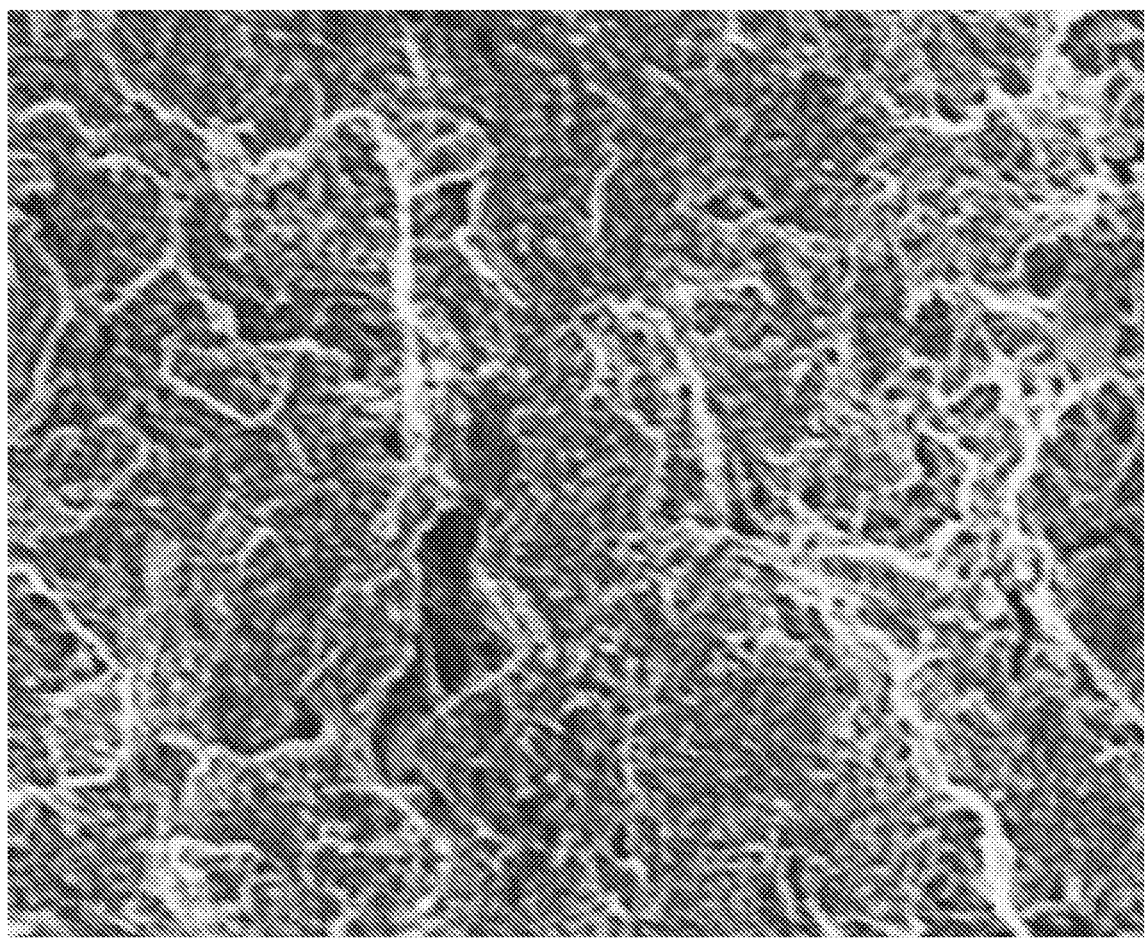
FIG. 9 is a scanning electron microscopy image of a working electrode having cysteine functionalized graphene oxide with polypyrrole (sGO/PPy).

Although the cysteine functionalized graphene oxide with polypyrrole nanocomposite working electrode 136 may be constructed in a number of different ways, one specific example is discussed herein. In this exemplary construction method, graphene oxide is utilized as a starting material. The cysteine functionalized graphene oxide is then synthesized using carbonyldiimidazole (CDI) via amide and carbamate linkage to obtain large numbers of cysteine moieties on the graphene oxide surface. Subsequently, the cysteine functionalized graphene oxide and polypyrrole is electrochemically grown on the working electrode to result in the desired working electrode. The cysteine functionalized graphene oxide with polypyrrole modified working electrode is illustrated in FIG. 9 in the form of a scanning electron microscopy (SEM) image.

FIGS. 10A and 10B illustrate a second embodiment of a detection device 200 configured to detect contaminants and pH of a fluid sample. The detection device 200 is similar to the detection device 100 shown and described with reference to FIGS. 1A and 1B. Accordingly, like features with the device 200 are shown with like reference numerals plus "100." For example, features 124, 128, 132, 136, 140, and 144 of FIG. 1A correspond to features 224, 228, 232, 236, 240, and 244 respectively of FIG. 10A. Features that are different from the device 100 above will be described in reference to FIGS. 10A and 10B. However, features presented with respect to FIGS. 10A and 10B may be incorporated into the embodiment illustrated in FIGS. 1A and 1B, and features presented above may be incorporated into the embodiment illustrated in FIGS. 10A and 10B.

With reference to FIG. 10A, the device 200 includes an electrode assembly 210, a control unit 220, and a microfluidic paper 250. The microfluidic paper 250 is configured to gather a fluid sample near a sample introduction end 254 and continuously transport the fluid sample through the microfluidic paper 250 via capillary action to a sample application area 258. When in use, the sample application area 258 is aligned with the electrode assembly 210 such that the sample application area 258 is located adjacent to the working area 248 during operation. In addition to transporting the fluid, the microfluidic paper 210 blocks particulates from the working area 248 and pre-concentrates contaminants, both of which enhance sensitivity of the device 200. In some constructions, the microfluidic paper 250 is made from a filter paper (e.g., Whatman filter paper, cellulose filter paper, etc.) that is functionalized with a material (sodium dodecylsulphate, glucose oxidase, etc.) to, among other things, improve mechanical properties of the paper 250 while retaining the microstructure of the paper 250—that is, the paper 250 is mechanically stronger while still retaining the ability to gather and transport liquid via capillary action. The microfluidic paper 250 may include a patterned hydrophobic barrier 262 (e.g., PDMS, wax, SU8, polystyrene, alkyl ketene dimer, etc.) inside of the microfluidic paper to guide the transport of the fluid sample to the working area. The microfluidic paper may also include an ion-exchange medium 266 (e.g., nafion, SDS, polythionine, polystyrene sulfonates (PSS), calcium, phosphate, amine-derivatives, sulfonic acid, carboxylic acid-derivatives, or any other suitable cation or anion exchange medium) that is configured to pre-concentrate the fluid sample before it reaches the working area. In some embodiments, the ion-exchange medium 266 is located in the sample application area 258.

With reference to FIG. 10B, the device may be utilized in spot testing applications (e.g., single test) or continuous testing applications. In the spot testing application, the device may be contained within a housing 270 supporting electrode assembly 210. In the illustrated embodiment, the housing 270 also supports the control unit 220 and detachably receives the microfluidic paper 250 (e.g., via slot 280). The microfluidic paper 250 may be configured to be reusable for a number of tests, or alternatively may be replaceable and/or disposable. In some embodiments, the microfluidic paper is supported within the housing 270 while a fluid sample is applied (e.g., to a portion of the microfluidic paper exposed outside of the housing). In other embodiments, the microfluidic paper 250 may be separable such that the user may gather a fluid sample with the paper 250, separate from the housing 270, and then introduce the paper 250 into the housing 270 for analysis. However, in other embodiments, the microfluidic paper 250 may be omitted such that the fluid sample is introduced to the working area 248 without the use of the microfluidic paper 250 (e.g., via an input of the housing 270 or the working area 248 may be exposed outside of the housing 270).

The device 200 also includes an input/output unit 290 coupled to the control unit 220 that is configured to display or output results such as pH level and contaminant concentrations. The contaminant concentrations may include both a contaminant identifier (e.g., lead, mercury, etc.) and a quantity (e.g., concentration (parts per million or parts per billion)). The input/output unit 290 may include a touch screen display implementing a graphical user interface (GUI) for receiving user commands and displaying results. The input/output unit 290 may further include a communications circuit for exporting results to and receiving commands from external devices (e.g., servers, laptops, mobile devices, tablets, etc.) via various wired and wireless communications formats. The input/output unit 290 may further include one or more other output devices (e.g., speakers, LEDs, vibration elements, etc.) to convey results and other device information visually, audibly, or via tactile feedback, and one or more other input devices (e.g., push buttons, toggle switches, microphones, etc.) to receive input from a user.

In operation, the microfluidic paper 250 has a fluid sample introduced through the sample introduction end 254 via contact with a fluid sample. This contact may be accomplished by a user delivering a fluid sample directly onto the microfluidic paper 250 (e.g., via a pipette), or by the user contacting the paper 250 with a fluid sample (e.g., by dipping the paper in a fluid sample). Once the paper 250 contacts the fluid sample, the fluid sample is wicked, via capillary action, through the microstructure of the paper 250. The paper is configured to transport the fluid sample through the paper 250 to the sample application area 258 such that the fluid is introduced to the working area 248 of the device 200. As noted above, the fluid may be guided by the hydrophobic barrier 262 and may also pass through the ion-exchange medium 266 before reaching the working area 248. Once the fluid sample has been delivered to the working area 248, the operation is substantially similar to the operation set forth above with respect to FIGS. 1A and 1B.

Figure 11:
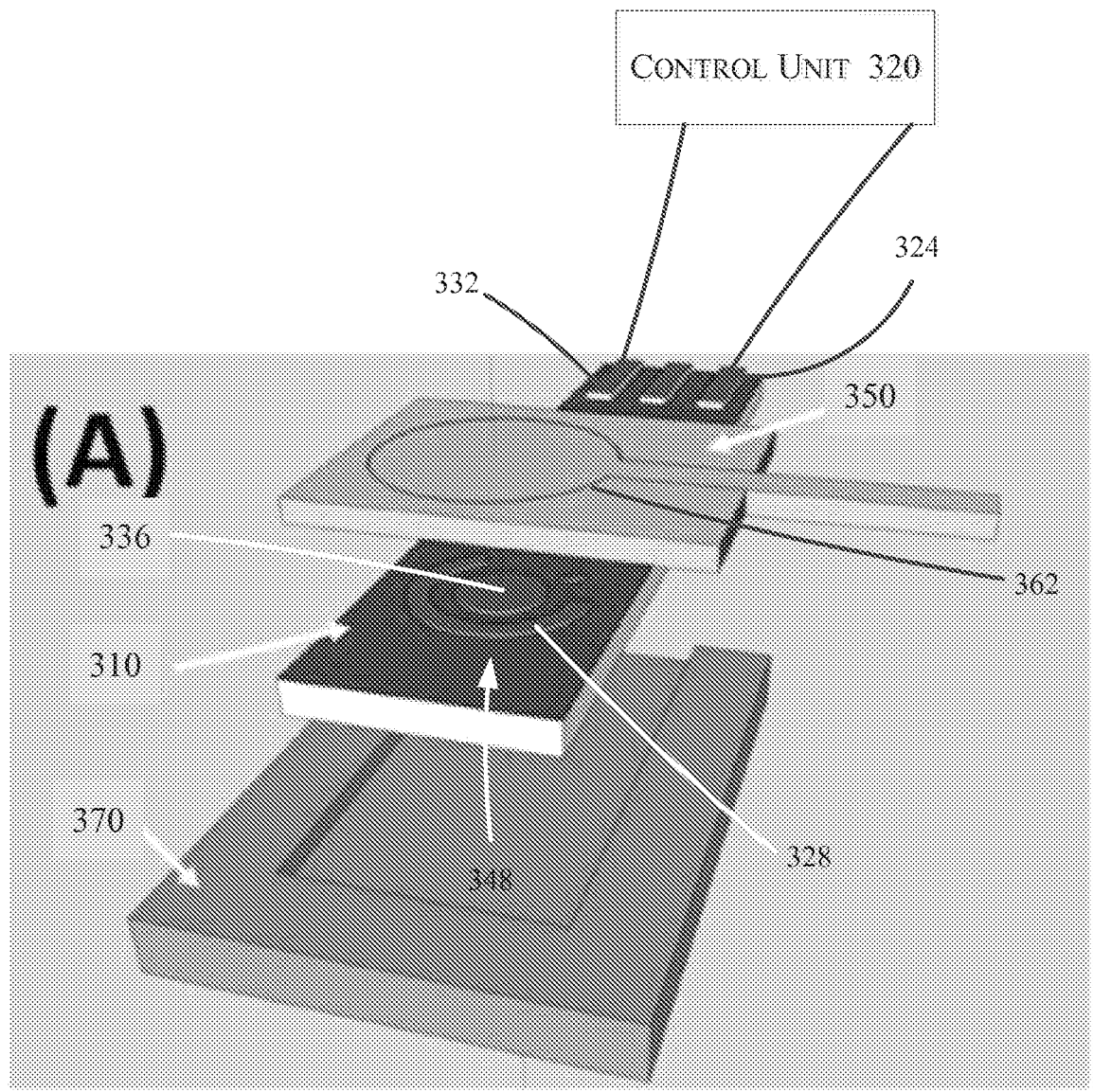
FIG. 11 is a plan view of a third contaminant detection device.

FIG. 11 illustrates yet another embodiment of a detection device 300 that is configured to detect the pH of a fluid sample. Features presented with respect to FIG. 11 may be incorporated into the embodiment illustrated in FIGS. 1A-1B and 10A-10B, and features presented above may be incorporated into the embodiment illustrated in FIG. 11.

With continued reference to FIG. 11, the detection device 300 includes a control unit 320, an electrode assembly 310, and a housing or holder 370. The electrode assembly 310 is supported within the holder 370 and includes a reference electrode 328 coupled to a first contact 324 and a working electrode 336 coupled to a second contact 332. Each of the first contact 324 and the second contact 332 are electrically coupled to the control unit 320. In one embodiment, at least one of the reference electrode 328 and the working electrode 336 may include an $H^+$ responsive material such as glass, metal oxides $MO_x$ (M=metal, x=different values for different valence states) or sometimes in the hydrated form $M(OH)_x$ (hydroxide) (e.g., $IrO_2$, $RuO_2$, $Al_2O_3$, $Ta_2O_5$, $PtO_2$, $Fe_2O_3$, CoO, $La_2O_3$, $TiO_2$, $SnO_2$, $WO_3$, $MoO_3$, $PbO_2$, $SrTiO_3$, etc.) or nitrides (e.g., $TiN_2$, $Si_3N_4$, AlN, GaN, etc.) with or without a scaffolding material (e.g., reduced graphene oxide, carbon nanotubes, carbon nanodots, silicon nanowires, fullerene, glassy carbon, activated carbon, etc.). In addition, at least one of the reference electrode 328 and the working electrode 336 may include Ag/AgCl, graphite/AgCl, standard hydrogen, Ag/AgI, or $IrO_2$, among other substances. Collectively, the reference electrode 328 and the working electrode 336 define a working area 348.

One exemplary construction of the working electrode 336 includes an iridium oxide-reduced graphene oxide ($IrO_2$-RGO) film on the working electrode 336. In this construction, the working electrode 336 has an irregular and rough surface (e.g., a screen printed graphitic carbon surface). The reduced graphene oxide aids in overcoming the typical irregular, rough working electrode 336 surface to form a smooth and good-standing anodically electrodeposited $IrO_2$ thin film. The resulting $IrO_2$-RGO modified working electrode 336 is highly sensitive and effective in measuring pH of a fluid sample.

The detection device 300 may also include a microfluidic paper device 350 that is supported by the holder 370. The microfluidic paper 350 is configured to gather a fluid sample, which may be a microfluidic sample (e.g., between approximately 0.1-500 µL or 20-180 µL) or any larger size (e.g., orders of magnitude larger), and continuously transport the fluid sample through the microfluidic paper 350 to the working area 348 via capillary action area, while also blocking particulates from the working area 348. In some constructions, the microfluidic paper 350 is made from a filter paper (e.g., Whatman No. 1 filter paper, cellulose filter paper, etc.) that is functionalized by with a material (sodium dodecylesulphate, glucose oxidase, etc.) to, among other things, improve mechanical properties of the paper 350 while retaining the microstructure of the paper 350. The microfluidic paper 350 may include a patterned hydrophobic barrier 362 (e.g., PDMS, wax, etc.) on the microfluidic paper to guide the transport of the fluid sample to the working area 348. Additionally, the microfluidic paper 350 continuously supplies the fluid sample to the working area 348 to achieve stable and reproducible readings.

In one construction, the hydrophobic barrier 362 is applied by placing a polydimethylsiloxane (PDMS) stamp onto the microfluidic paper 350 with a vacuum cover subsequently located on the opposite side of the stamp across the paper 350. A vacuum is then applied by the cover for a predetermined amount of time (e.g., 30 seconds) to apply the PDMS to the stamp in a specific pattern such than an inner hydrophilic region is maintained. The paper 350 is then heated to harden the patterned PDMS.

In operation, the fluid sample is received in the working area 348 either by complete immersion of the working area 348 within the fluid sample, user delivery of the fluid sample to a working area 348, or fluid sample delivery utilizing the microfluidic paper 348. Then, the control unit 320 measures an open circuit potential between the reference electrode 328 and the working electrode 336. The resulting open circuit potential is proportional to the $H^+$ ion concentration of the fluid sample (i.e., the pH) such that the control unit 320 can determine the pH of the fluid sample based on the measured open circuit potential. In some embodiments, the control unit 320 is configured to display a digital readout of the pH on a GUI associated with the device 300.

Figure 12A:
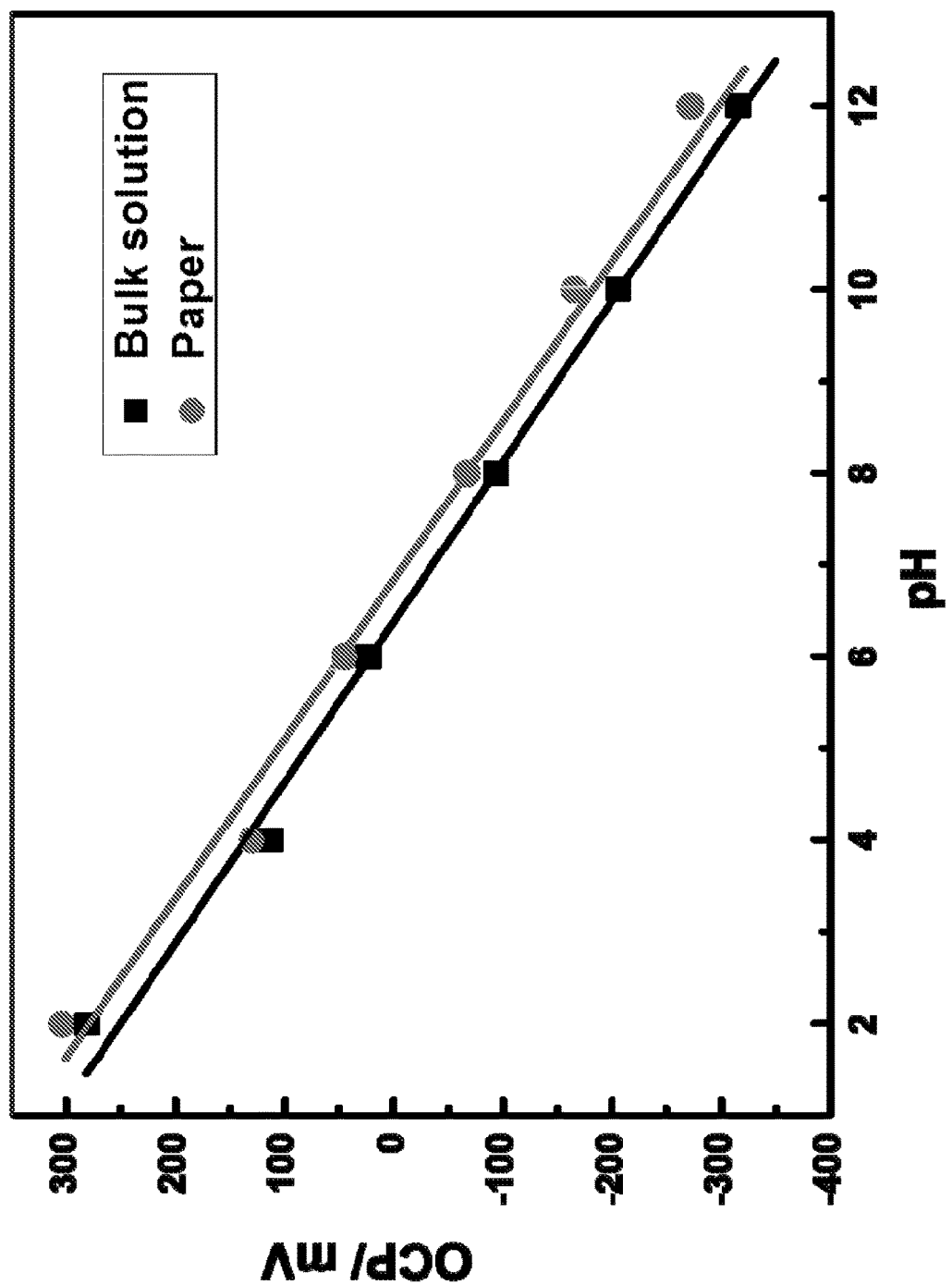
FIG. 12A is a graph of open circuit potential, measured using the device of FIG. 11, vs pH illustrating the pH responses of the device at different pH values.
Figure 12B:
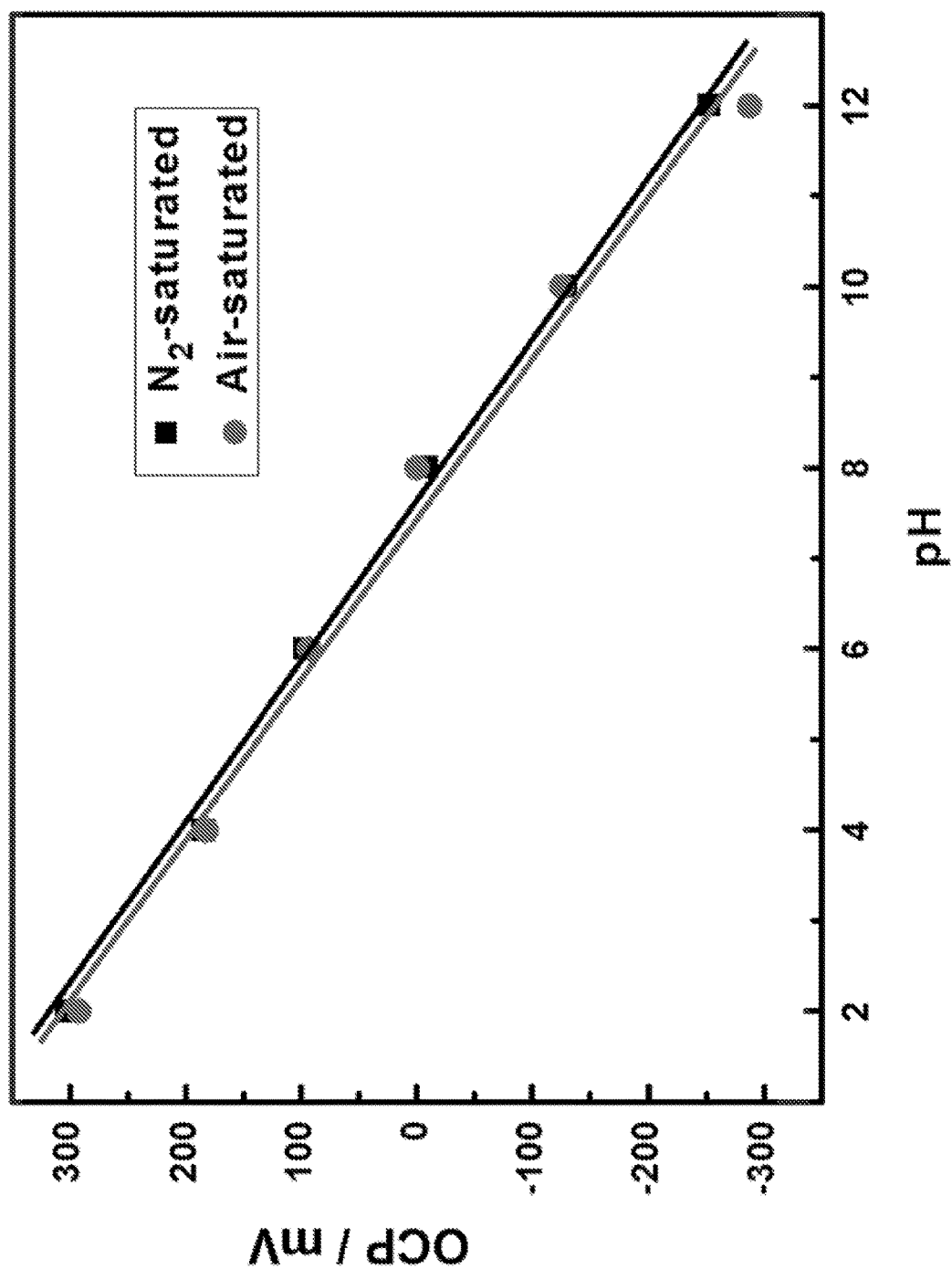
FIG. 12B is a graph of open circuit potential, measured using the device of FIG. 11, vs pH illustrating the pH response of the device in fluid samples saturated with air or $N_2$.
Figure 12C:
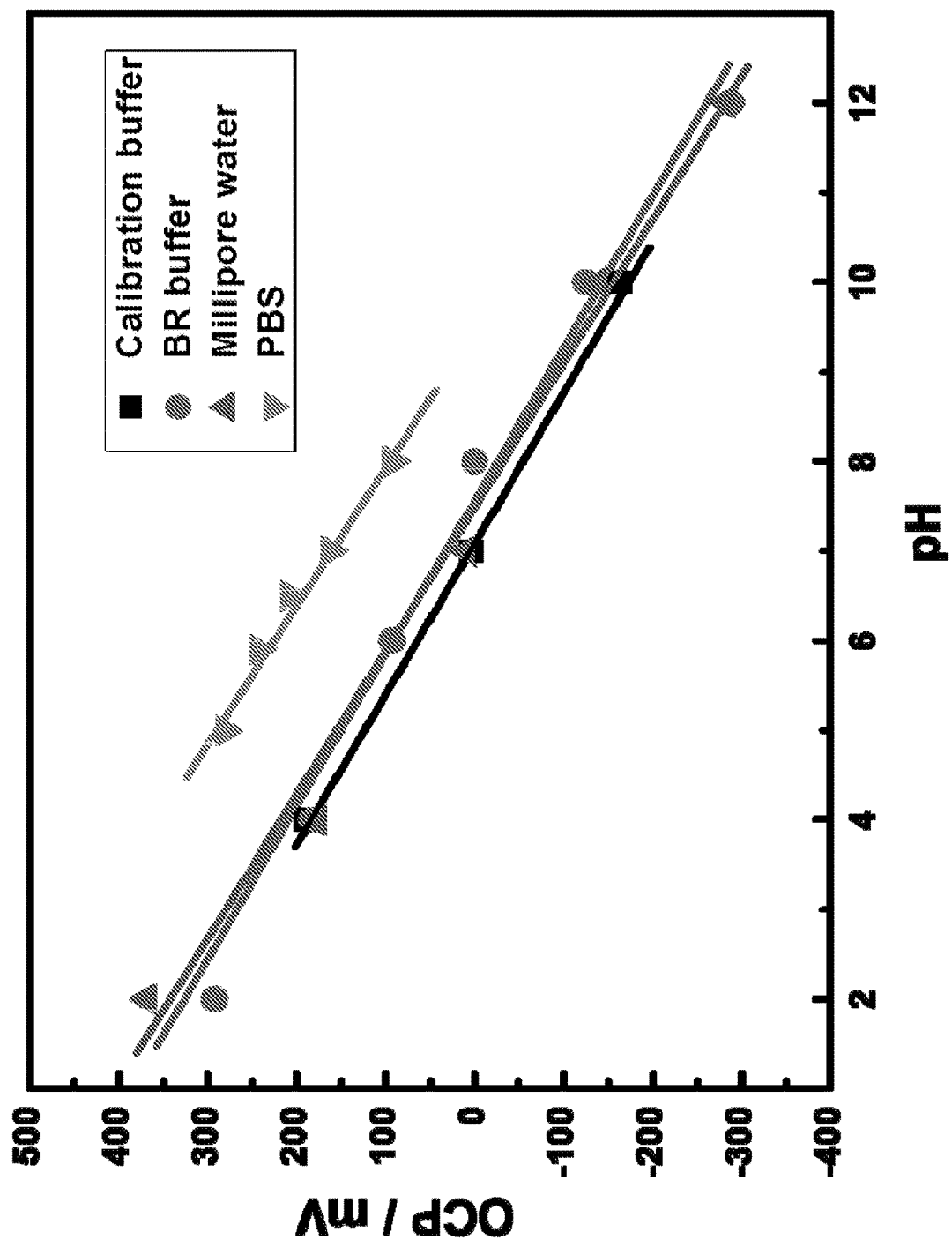
FIG. 12C is a graph of open circuit potential, measured using the device of FIG. 11, vs pH illustrating the pH response of the device in different buffer solutions.

FIGS. 12A-12C illustrate performance characteristics of the exemplary $IrO_2$-RGO working electrode 336 used in the device 300. The $IrO_2$-RGO working electrode 336 exhibits a well-defined linear characteristic over a wide pH range from 2 to 12 (FIG. 12A). Advantageously, the $IrO_2$-RGO working electrode 336 is generally unaffected by dissolved atmospheric oxygen, $N_2$—, or air-saturated buffer solutions, which can influence operational performance of the working electrode 336 when measuring pH due to reduction processes. FIG. 12B illustrates the fact that there are only minor differences in the performance of the $IrO_2$-RGO working electrode 336 when dissolved atmospheric oxygen, $N_2$—, or air-saturated buffer solutions are present. Furthermore, the $IrO_2$-RGO working electrode 336 is generally unaffected by different ionic species. As evidenced by FIG. 12C, the $IrO_2$-RGO working electrode 336 is generally unaffected by different fluid samples (e.g., commercial pH calibration buffer, B—R buffer, phosphate buffered saline (PBS) and NaOH/HCl adjusted Millipore water). Additionally, the sensitivities (mV per pH unit) are similar in each of the buffers.

Figure 13A:
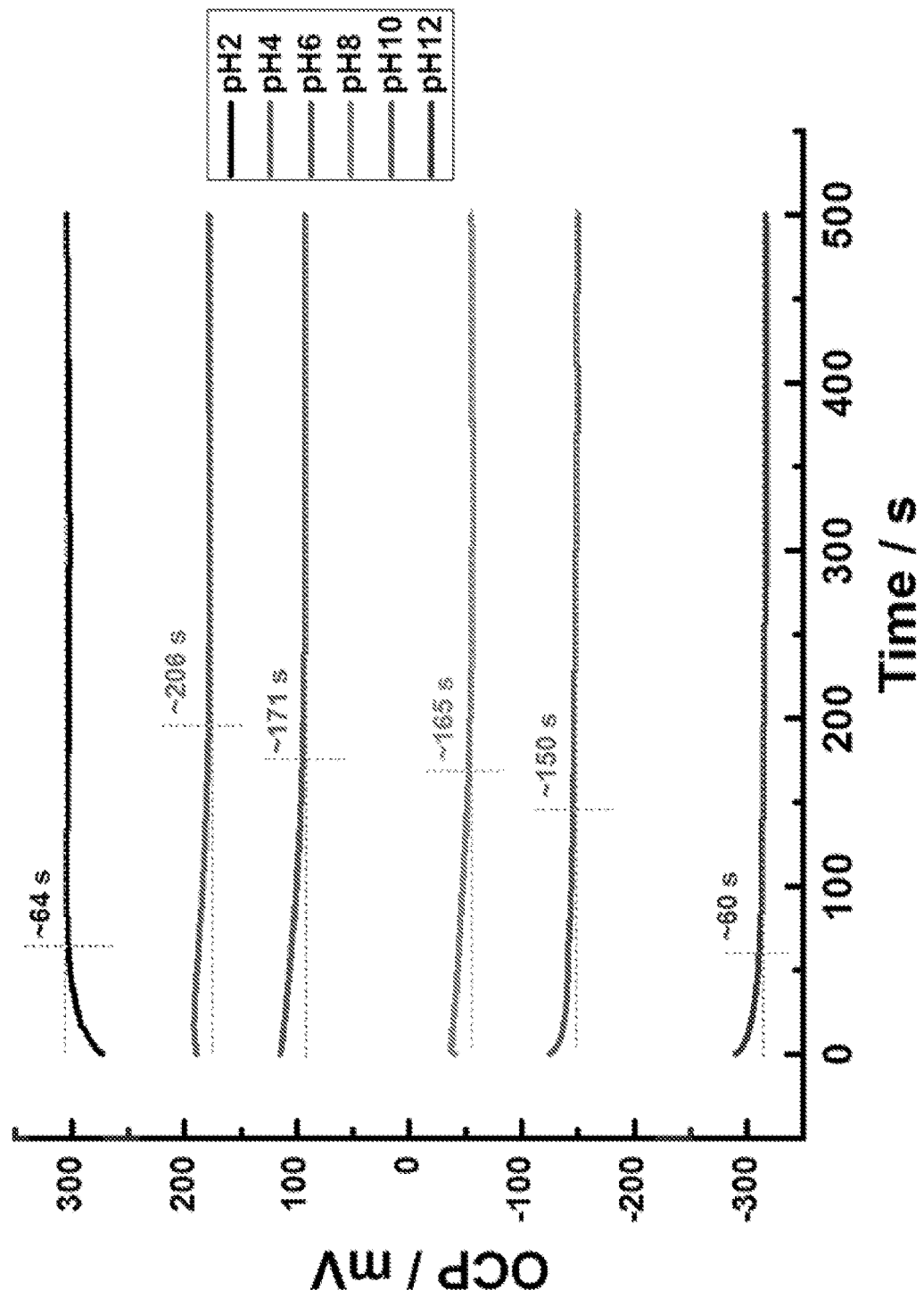
FIG. 13A is a graph of open circuit potential vs. time for the device of FIG. 11 in fluid samples having pH 2, 4, 6, 8, 10 and 12 to illustrate response times of the device.
Figure 13B:
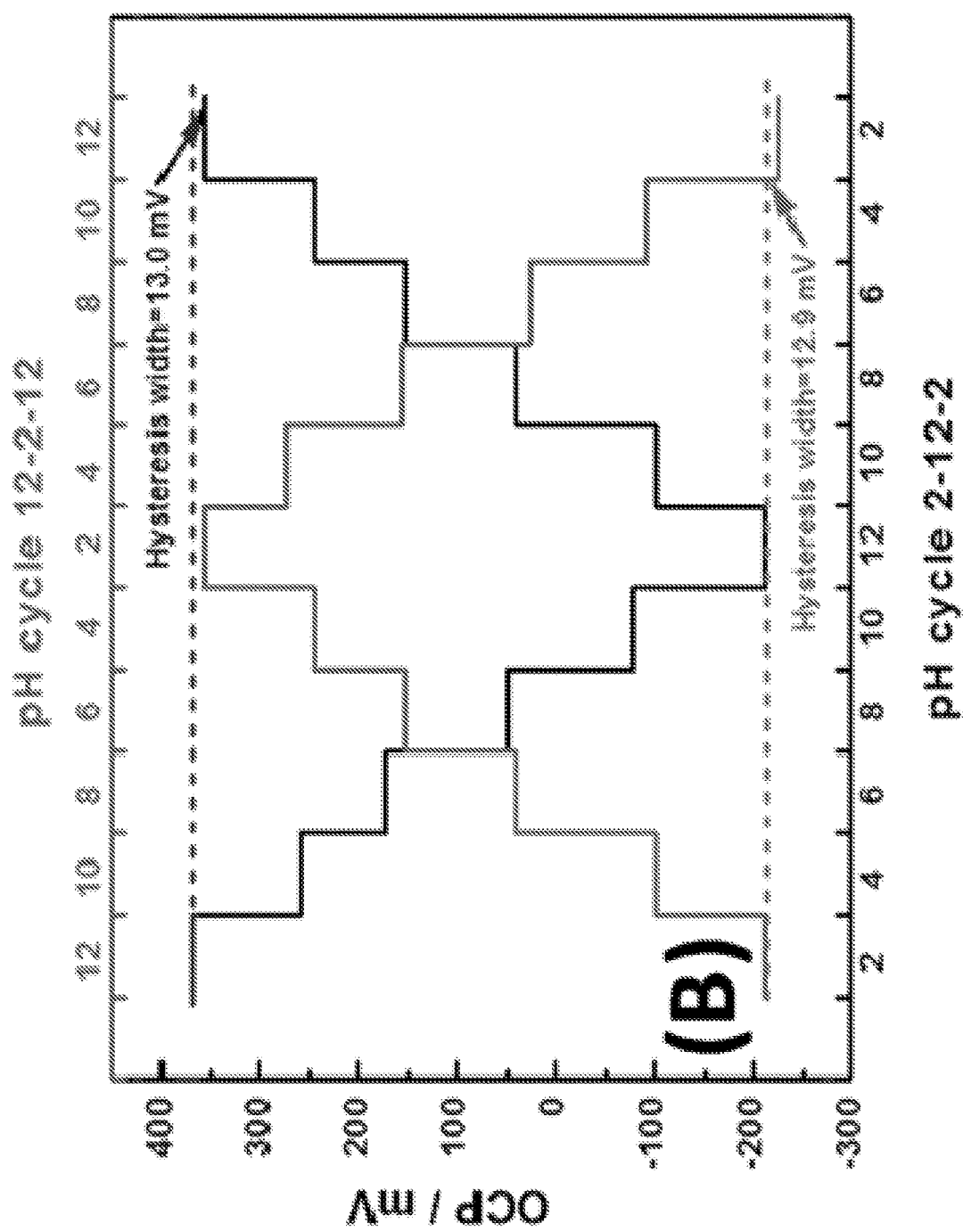
FIG. 13B is a graph of graph of open circuit potential vs. pH cycle 2-12-2 and pH cycle 12-2-12 to illustrate hysteresis widths of the device.

FIG. 13A-13B illustrate additional performance characteristics of the exemplary $IrO_2$-RGO working electrode 336 used in the device 300. One such characteristic, response time, is a factor in sensing applications. Response time is usually defined as the time required to reach certain percentages of equilibrium open circuit potential in order to achieve a stable pH reading. In the example, typical response time is less than about 200 s in all pH settings. Another characteristic of the exemplary $IrO_2$-RGO working electrode 336 used in the device 300 is hysteresis, or the so-called memory effect, which is a known phenomenon with glass and metal oxide pH electrodes existing during repetitive uses of the same electrode. This phenomenon of hydrogen ion-selective electrodes is considered as the result of delayed pH responses. The IrO2-RGO working electrode 336 was tested in pH buffers in turn from low to high, and from high to low alternately. Loop cycles of pH 2-12-2 and 12-2-12 were assessed by successively measuring open circuit potential of different pH buffers in the cycles (FIG. 13B). The hysteresis widths are calculated to be around 13 mV in both cycles, which are acceptable and accurate in routine pH measurements, particularly regarding the wide pH range studied.

Figure 14:
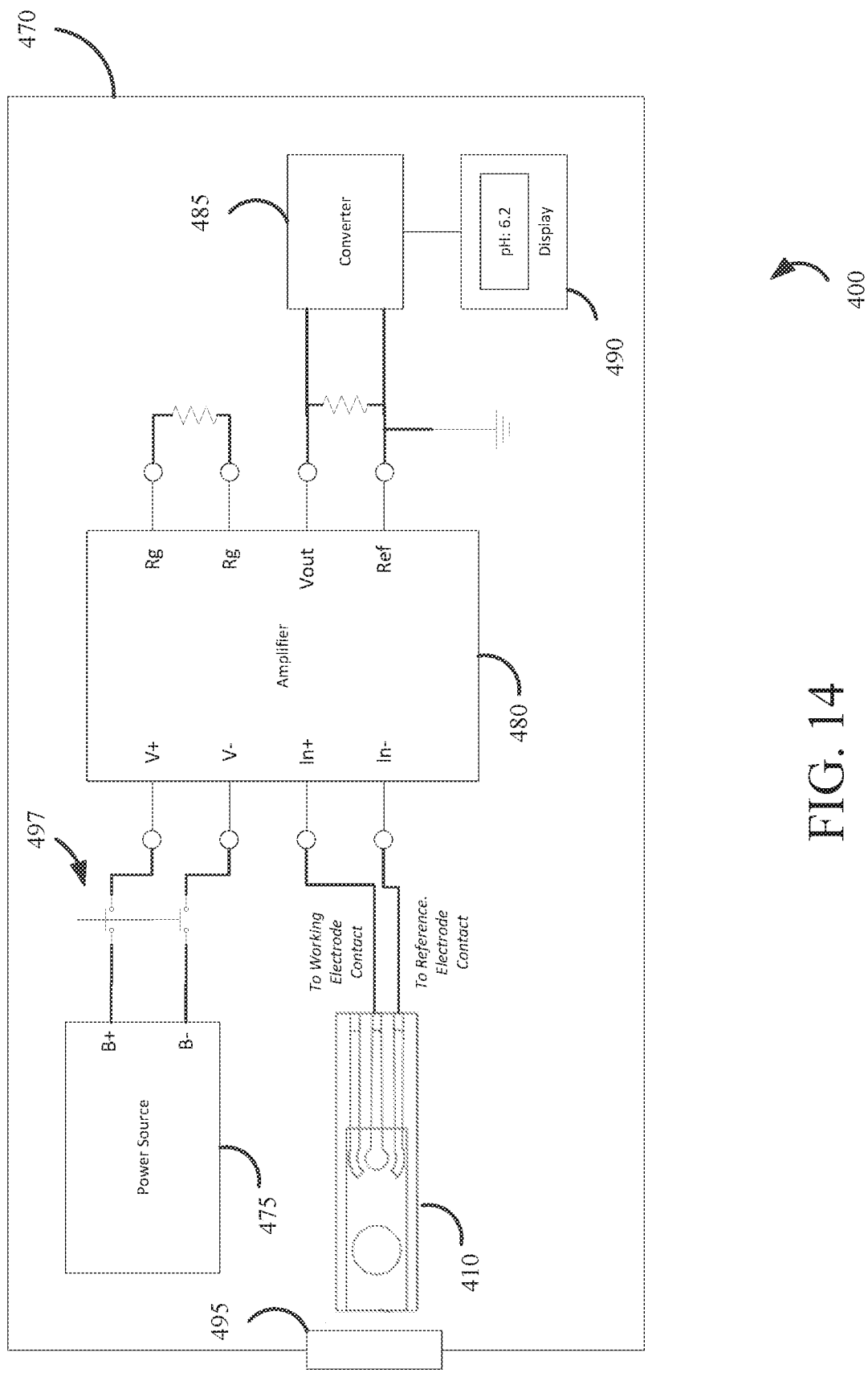
FIG. 14 is a plan view of a fourth contaminant detection device.

FIG. 14 illustrates another embodiment of a detection device 400 configured to detect the pH of a fluid sample. The detection device 400 is similar to the detection device 200 shown and described with reference to FIGS. 10A-10B. Accordingly, like features with the device 200 are shown with like reference numerals plus "200." Features that are different from the device 200 above will be described in reference to FIG. 14. However, features presented with respect to FIG. 14 may be incorporated into the embodiment illustrated in FIGS. 10A-10B, and features presented above may be incorporated into the embodiment illustrated in FIG. 14.

With reference to FIG. 14, the device 400 includes an electrode assembly 410 operable to receive a fluid sample. The device 400 may be utilized in spot testing applications (e.g., single test) or continuous testing applications. The device 400 may be a handheld, portable device that is contained within a housing 470 supporting electrode assembly 410. In the illustrated embodiment, the housing 470 also supports a power source 475, an amplifier 480, a converter 485, and a display 490. The housing further includes a slot 495 for receipt of a microfluidic paper, similar to microfluidic paper 250 noted above, for delivery of the fluid sample to the electrode assembly 410. In some embodiments, the microfluidic paper may be omitted such that the fluid sample is introduced to a working area of the electrode assembly 410 without the use of the microfluidic paper (e.g., via an input of the housing 470 or the working area may be exposed outside of the housing 470).

The power source 475 may include one or more standard primary batteries (e.g., two 9-volt batteries) or secondary (rechargeable) batteries providing a positive and negative power supply voltage to pins of the amplifier 480. Alternatively, the device 400 may be powered by an alternative current (AC) power source, receiving power via a cord coupled to a typical AC wall outlet. In such embodiments, the power source 475 may include a rectifier, filter, and other conditioning circuitry to provide direct current (DC) power to the components of the device 400.

A pushbutton 497 may be, for instance, provided on an exterior of the housing 470 for manipulation by a user to turn the device 400 on and off. When the pushbutton 497 is toggled on, power is provided to the amplifier 480, the converter 485 (via a path not shown), and the display 490 (via a path not shown). The amplifier 480, when powered, amplifies the signal received at input pins In+ and In−, providing the amplified signal as an analog voltage output at an output pin Vout. As but one example, the amplifier 480 may be a high speed FET-Input Instrumentation Amplifier, such as INA111 offered by Burr-Brown®.

The converter 485 receives the analog voltage output and converts the voltage to a pH level, e.g., using a look-up table stored in a memory of the converter 485. The voltage-to-pH level relationship may be generally linear, such as shown in FIG. 12A, with 300 mV voltage output from the amplifier 480 indicating an approximate pH level of 2, and a −300 mV voltage output indicating an approximate pH level of 12. The particular plot shown in FIG. 12A is merely exemplary, as the particular relationship and scale of voltage-to-pH level may vary dependent on the particular amplifier chosen, materials of the electrode assembly 410, among other factors. The converter 485 provides the determined pH level to the display 490, which may be, for example, a liquid crystal display (LCD). The display 490, in turn, displays the pH level of the fluid sample. The display 490 may be provided on an exterior of the housing such that the output pH level is viewable by a user.

Various features of the invention are set forth in the following claims.

What is claimed is:

1. A device for measuring the concentration of contaminants within a fluid sample, the device comprising:
   a power source; and
   a control unit electrically coupled to the power source, the control unit being configured to supply an input signal to measure a corresponding output signal from an electrode assembly that includes
   a first contact electrically coupled to a reference electrode,
   a second contact electrically coupled to a cysteine functionalized graphene oxide with polypyrrole nanocomposite modified working electrode, and
   a third contact electrically coupled to a counter electrode;
   wherein the output signal is indicative of contaminant concentration within the fluid sample,
   wherein the input signal includes a first, fixed potential that is applied across the cysteine functionalized graphene oxide with polypyrrole nanocomposite modified working electrode and the reference electrode in order to adhere a plurality of contaminant ions to the cysteine functionalized graphene oxide with polypyrrole nanocomposite modified working electrode, and a second, varied potential, applied after the first fixed potential, across the cysteine functionalized graphene oxide with polypyrrole nanocomposite modified working electrode and the reference electrode in order to remove the contaminant ions from the cysteine functionalized graphene oxide with polypyrrole nanocomposite modified working electrode, and wherein the output signal is a change in electrical current flowing between the cysteine functionalized graphene oxide with polypyrrole nanocomposite modified working electrode and the counter electrode as the contaminant is adhered to and removed from the cysteine functionalized graphene oxide with polypyrrole nanocomposite modified working electrode.

2. The device of claim 1, wherein the electrode assembly is a screen printed electrode.

3. The device of claim 1, wherein the device is configured to detect multiple contaminant species simultaneously.

4. The device of claim 1, wherein the contaminants include arsenic, lead, copper, cadmium, mercury, chromium, iron, zinc, barium, bromine, and fluoride.

5. The device of claim 1, wherein device is configured to be a handheld, portable device.

6. The device of claim 1, wherein the control unit is configured to measure a concentration of contaminants within a fluid using anodic stripping voltammetry.

7. The device of claim 1, wherein the control unit is configured to measure a contaminant concentration based on the output signal.

8. The device of claim 1, further comprising a microfluidic paper filter configured to wick the fluid sample and transport the fluid sample into contact with the electrode assembly.

9. The device of claim 8, wherein the microfluidic paper includes an ion-exchange medium doped filter paper configured to concentrate the fluid sample before the fluid sample contacts the electrode assembly.

10. The device of claim 9, wherein the ion-exchange medium includes nafion.

11. An electrode assembly for measuring the concentration of contaminants within a fluid sample, the electrode assembly comprising:
    a first contact electrically coupled to a reference electrode;
        a second contact electrically coupled to a cysteine-functionalized graphene oxide with polypyrrole modified working electrode; and
        a third contact electrically coupled to a counter electrode,
        wherein the electrode assembly is configured to receive an input signal that includes a first, fixed potential that is applied across the cysteine functionalized graphene oxide with polypyrrole nanocomposite modified working electrode and the reference electrode in order to adhere a plurality of contaminant ions to the cysteine functionalized graphene oxide with polypyrrole modified working electrode, and a second, varied potential, applied after the first fixed potential, across the cysteine functionalized graphene oxide with polypyrrole nanocomposite modified working electrode and the reference electrode in order to remove the contaminant ions from the cysteine functionalized graphene oxide with polypyrrole modified working electrode,
        wherein the electrode assembly is configured to provide an output signal that is indicative of contaminant concentration within the fluid sample, and
        wherein the output signal is a change in electrical current flowing between the cysteine functionalized graphene oxide with polypyrrole nanocomposite modified working electrode and the counter electrode as the contaminant is adhered to and removed from the cysteine functionalized graphene oxide with polypyrrole nanocomposite modified working electrode.

12. The electrode of claim 11, wherein the contaminants include arsenic, lead, copper, cadmium, mercury, chromium, iron, zinc, barium, bromine, and fluoride.

13. The electrode of claim 11, wherein the electrode assembly is a screen printed electrode.

14. A method for measuring contaminant concentration within a fluid sample using a contaminant detection device including an electrode assembly and a control unit, the method comprising:
    contacting, by the fluid sample, the electrode assembly, the electrode assembly including a reference electrode, a measurement electrode having a cysteine functionalized graphene oxide with polypyrrole nanocomposite, and a counter electrode;
    applying a first electrical signal to the measurement electrode from the control unit;
    applying a second electrical signal to the measurement electrode from the control unit;
    measuring an output signal indicating a change in electrical current between the counter electrode and the measurement electrode with the control unit while applying the second electrical signal;
    measuring a circuit potential of the electrode assembly using the control unit in order to determine a pH of the fluid sample; and
    determining a contaminant concentration based on the output signal by correlating the output to the contaminant concentration within the fluid sample based on the pH of the fluid sample.

15. The device of claim 14, wherein contacting the electrode assembly includes at least one of completely immersing the electrode assembly in the fluid sample or placing an amount of fluid sample into contact with the electrode assembly.

16. The method according to claim 14, further comprising pre-concentrating a fluid sample using a microfluidic paper filter prior to contacting, by the fluid sample, the electrode assembly.

17. The method of claim 16, wherein the microfluidic paper filter includes an ion-exchange medium doped filter paper that pre-concentrates the fluid sample.

18. The method of claim 17, wherein the ion-exchange medium includes nafion.

19. The method of claim 14,
    wherein the first electrical signal is reducing potential applied to the measurement electrode,
    wherein the second electrical signal is a varied potential that moves from the reducing potential to an oxidizing potential,
    wherein applying the first electrical signal includes depositing the contaminant within the fluid sample onto the measurement electrode, and
    wherein applying the second electrical signal includes stripping the contaminant within the fluid sample from the measurement electrode.

* * * * *